United States Patent
Nesvadba et al.

(10) Patent No.: US 7,199,245 B2
(45) Date of Patent: Apr. 3, 2007

(54) 4-IMINO-N-ALKOXY OR OXY-POLYALKYL-PIPERIDINE COMPOUNDS AND THEIR USE AS POLYMERIZATION REGULATORS

(75) Inventors: Peter Nesvadba, Marly (CH); Tobias Hintermann, Basel (CH); Andreas Kramer, Meyriez (CH); Marie-Odile Zink, Mulhouse (FR); Lucienne Bugnon, Pfeffingen (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 302 days.

(21) Appl. No.: 10/480,188

(22) PCT Filed: Jun. 4, 2002

(86) PCT No.: PCT/EP02/06108

§ 371 (c)(1),
(2), (4) Date: Dec. 9, 2003

(87) PCT Pub. No.: WO02/100831

PCT Pub. Date: Dec. 19, 2002

(65) Prior Publication Data

US 2004/0176553 A1    Sep. 9, 2004

(30) Foreign Application Priority Data

Jun. 13, 2001   (EP) ................................. 01810567
Nov. 28, 2001   (EP) ................................. 01811154

(51) Int. Cl.
    *C07D 401/02*   (2006.01)
(52) U.S. Cl. ........................ 546/201; 546/205; 546/208; 546/222; 546/224; 546/242; 546/244; 526/328.5; 526/217; 526/328
(58) Field of Classification Search ................ 546/201, 546/205, 208, 222, 224, 242, 244; 526/328.5, 526/217, 328; 44/275; 252/405; 524/99
See application file for complete search history.

(56) References Cited

U.S. PATENT DOCUMENTS 3,503,982 A * 3/1970 Morimura et al. ............ 546/16
6,353,107 B1   3/2002 Kramer et al. ............. 546/216
6,479,608 B1  11/2002 Nesvadba et al. ....... 526/328.5
6,624,306 B2   9/2003 Nesvadba et al. .......... 546/201
6,755,875 B2 *  6/2004 Wood et al. ................. 44/275

FOREIGN PATENT DOCUMENTS

GB    1076700    7/1967
GB    2335190    9/1999

OTHER PUBLICATIONS

V. Gadjeva et al, Pharmazie, vol. 54, No. 3, (1999), pp. 231-232.
J. Martinez de Ilarduya et al., Polish Journal of Chemistry, vol. 65, pp. 2251-2258, (1991).
Kolloidn. ZH. vol. 53, No. 1, (1991), pp. 109-113.
Chemical Abstract vol. 82, No. 22, (1975), 141108w for JP 7440557.
H. Tanaka et al., Bulletin of the Chemical Society of Japan, vol. 51 (9), pp. 2451-2455, (1978).

* cited by examiner

*Primary Examiner*—Robert D. Harlan
(74) *Attorney, Agent, or Firm*—Tyler A. Stevenson

(57) ABSTRACT

The present invention relates to selected 4-imino-N-alkoxy-polyalkyl-peperidine compounds preparation, a polymerizable composition comprising a) at least one ethylenically unsaturated monomer and b) a 4-imino-N-alkoxy-polyalkyl-piperidine compound. Further aspects of the present invention are a process for polymerizing ethylenically unsaturated monomers, and the use of 4-imino-N-alkoxy-polyalkyl-piperidine compounds for controlled polymerization. The intermediate N-oxyl derivatives, a composition of the N-oxyl derivatives with ethylenically unsaturated monomers and a free radical initiator, as well as a process for polymerization are also subjects of the present invention

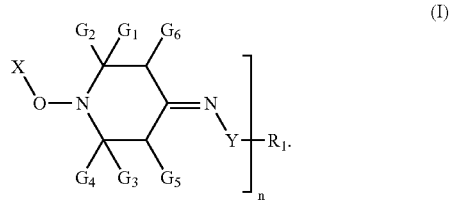

(I)

22 Claims, No Drawings

4-IMINO-N-ALKOXY OR OXY-POLYALKYL-PIPERIDINE COMPOUNDS AND THEIR USE AS POLYMERIZATION REGULATORS

The present invention relates to selected 4-imino-N-alkoxy-polyalkyl-piperidine compounds, a polymerizable composition comprising a) at least one ethylenically unsaturated monomer and b) a 4-imino-N-alkoxy-polyalkyl-piperidine compound. Further aspects of the present invention are a process for polymerizing ethylenically unsaturated monomers, and the use of 4-imino-N-alkoxy-polyalkyl-piperidine compounds for controlled polymerization. The intermediate N-oxyl derivatives, a composition of the N-oxyl derivatives with ethylenically unsaturated monomers and a free radical initiator, as well as a process for polymerization are also subjects of the present invention.

The compounds of the present invention provide polymeric resin products having low polydispersity. The polymerization process proceeds with good monomer to polymer conversion efficiency. In particular, this invention relates to stable free radical-mediated polymerization processes which provide homopolymers, random copolymers, block copolymers, multiblock copolymers, graft copolymers and the like, at enhanced rates of polymerization and enhanced monomer to polymer conversions.

U.S. Pat. No. 4,581,429 to Solomon et al., issued Apr. 8, 1986, discloses a free radical polymerization process which controls the growth of polymer chains to produce short chain or oligomeric homopolymers and copolymers, including block and graft copolymers. The process employs an initiator having the formula (in part) R'R"N—O—X, where X is a free radical species capable of polymerizing unsaturated monomers. The reactions typically have low conversion rates. Specifically mentioned radical R'R"N—O. groups are derived from 1,1,3,3 tetraethylisoindoline, 1,1,3,3 tetrapropylisoindoline, 2,2,6,6 tetramethylpiperidine, 2,2,5,5 tetramethylpyrrolidine or di-t-butylamine. However, the suggested compounds do not fulfill all requirements. particularly the polymerization of acrylates does not proceed fast enough and/or the monomer to polymer conversion is not as high as desired.

GB 2335190 firstly discloses polymerization regulators/initiators on the basis of 4-substituted 2,2,6,6-tetraalkylpiperidine, wherein the alkyl groups have from 1 to 4 carbon atoms and at least one group is different from methyl.

However none of the nitroxide and nitroxylether compounds, in particular none of those described as regulators/initiators for controlled radical polymerization have a 4-imino substitutent.

Surprisingly it has now been found that the 4-imino 2,2,6,6-tetraalkylpiperidine derivatives of the present invention are of particular industrial value, since they can be prepared in high yield and purity even considering large production quantities.

The imino structure in 4 position ensures high thermal stability which is important for storage, particularly at elevated temperatures.

The compounds exhibit an unchanged initiating/regulating activity even after storage at elevated temperatures as for example used in conventional stability tests.

Another problem associated with nitroxyl or nitroxyl ether mediated free radical polymerization is the formation of a significant color of the resulting polymer. The compounds of the present invention which have a imino structure in 4-position impart significantly less color to the polymer compared to other prior art compounds of similar structure.

In some cases either the end product or at least an intermediate product is of crystalline form and therefore can be easily purified by conventional recrystallization.

The 4-imino group surprisingly leads to slightly higher monomer to polymer conversions in some cases as compared to the corresponding 4-oxo group.

The steric hindrance introduced by ethyl groups instead of methyl groups in the 2 and/or 6 position further leads to an increased initiating activity and control of polymerization.

Furthermore, when the 4-hydroxylamine substitution is left as such, it is possible to react the OH group, when the polymer is already formed, to produce telechelics.

One subject of the invention is a compound of formula (I)

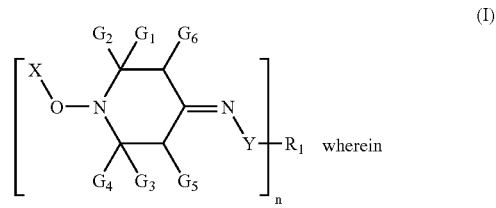

(I)

wherein $G_1$, $G_2$, $G_3$ and $G_4$ are independently $C_1$–$C_4$alkyl or $G_1$ and $G_2$ together and $G_3$ and $G_4$ together, or $G_1$ and $G_2$ together or $G_3$ and $G_4$ together are pentamethylene; wherein, when $G_1$, $G_2$, $G_3$ and $G_4$ are $C_1$–$C_4$alkyl, at least one is higher alkyl than methyl; $G_5$ and $G_6$ are each independently of the other hydrogen or $C_1$–$C_4$alkyl;

n is 1, 2, 3, or 4

Y is O, $NR_2$ or when n is 1 and $R_1$ represents alkyl or aryl Y is additionally a direct bond; $R_2$ is H, $C_1$–$C_{18}$alkyl or phenyl;

if n is 1

$R_1$ is H, straight or branched $C_1$–$C_{18}$alkyl, $C_3$–$C_{18}$alkenyl or $C_3$–$C_{18}$alkinyl, which unsubstituted or substitued, by one or more OH, $C_1$–$C_8$alkoxy, carboxy, $C_1$–$C_8$alkoxycarbonyl;

$C_5$–$C_{12}$cycloalkyl or $C_5$–$C_{12}$cycloalkenyl;

phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy, $C_1$–$C_8$alkoxycarbonyl;

—C(O)—$C_1$–$C_{36}$alkyl, or an acyl moiety of α,β-unsaturated carboxylic acid having 3 to 5 carbon atoms or of an aromatic carboxylic acid having 7 to 15 carbon atoms;

—$SO_3^-Q^+$, —$PO(O^-Q^+)_2$, —$P(O)(OR_2)_2$, —$SO_2$—$R_2$, —CO—NH—$R_2$, —$CONH_2$, $COOR_2$, or $Si(Me)_3$, wherein $Q^+$ is $H^+$, ammnonium or an alkali metal cation;

if n is 2

$R_1$ is $C_1$–$C_{18}$alkylene, $C_3$–$C_{18}$alkenylene or $C_3$–$C_{18}$alkinylene, which may be unsubsti substitued, by one or more OH, $C_1$–$C_8$alkoxy, carboxy, $C_1$–$C_8$alkoxycarbonyl;

or xylylene; or $R_1$ is a bisacyl radical of an aliphatic dicarboxylic acid having 2 to 36 carbon atoms, or a cycloaliphatic or aromatic dicarboxylic acid having 8–14 carbon atoms;

if n is 3, $R_1$ is a trivalent radical of an aliphatic, cycloaliphatic or aromatic tricarboxylic acid;

if n is 4, $R_1$ is a tetravalent radical of an aliphatic, cycloaliphatic or aromatic tetracarboxylic acid; and X is selected from the group consisting of
—CH-aryl,

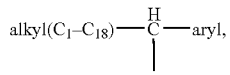

—CH$_2$—CH$_2$-aryl,

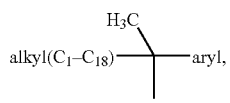

(C$_5$–C$_6$cycloalkyl)$_2$CCN, (C$_1$–C$_{12}$alkyl)$_2$CCN, —CH$_2$CH=CH$_2$, (C$_1$–C$_{12}$)alkyl-CR$_{20}$—C(O)—(C$_1$–C$_{12}$)alkyl, (C$_1$–C$_{12}$)alkyl-CR$_{20}$—C(O)—(C$_6$–C$_{10}$)aryl, (C$_1$–C$_{12}$)alkyl-CR$_{20}$—C(O)—(C$_1$–C$_{12}$)alkoxy, (C$_1$–C$_{12}$)alkyl-CR$_{20}$—C(O)-phenoxy, (C$_1$–C$_{12}$)alkyl-CR$_{20}$—C(O)—N-di(C$_1$–C$_{12}$)alkyl, (C$_1$–C$_{12}$)alky$_{20}$—CO—NH(C$_1$–C$_{12}$)alkyl, (C$_1$–C$_{12}$)alkyl-CR$_{20}$—CO—NH$_2$, —CH$_2$CH=CH—CH$_3$, —CH$_2$—C(CH$_3$)=CH$_2$, —CH$_2$—CH=CH-phenyl,

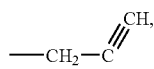

3–Cyclohexenyl, 3-cyclopentenyl,

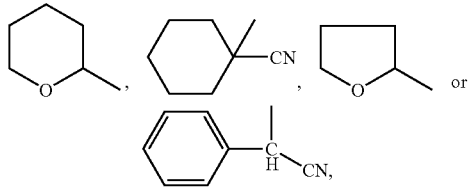

wherein
R$_{20}$ is hydrogen or C$_1$–C$_{12}$alkyl;
the alkyl groups are unsubstituted or substituted with one or more —OH, —COOH or —C(O)R$_{20}$ groups; and
the aryl groups are phenyl or naphthyl which are unsubstituted or substituted with C$_1$–C$_{12}$alkyl, halogen, C$_1$–C$_{12}$alkoxy, C$_1$–C$_{12}$alkylcarbonyl, glycidyloxy, OH, —COOH or —COO(C$_1$–C$_{12}$)alkyl.

C$_1$–C$_{18}$alkyl can be linear or branched. Examples are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl or octadecyl. Where up to C$_{36}$alkyl is possible, C$_1$–C$_{18}$alkyl is preferred.

Alkyl substituted by a group —COOH is for example CH$_2$—COOH, CH$_2$—CH$_2$—COOH, (CH$_2$)$_3$—COOH or CH$_2$—CHCOOH—CH$_2$—CH$_3$ Hydroxyl- or alkoxycarbonyl substituted C$_1$–C$_{18}$alkyl can be, for example, 2-hydroxyethyl, 2-hydroxypropyl, methoxycarbonylmethyl or 2-ethoxycarbonylethyl.

Alkenyl having from 3 to 18 carbon atoms is a branched or unbranched radical, for example propenyl, 2-butenyl, 3-butenyl, isobutenyl, n-2,4pentadienyl, 3-methyl-2-butenyl, n-2-octenyl, n-2-dodecenyl, isododecenyl.

Alkinyl having from 3 to 18 carbon atoms is a branched or unbranched radical, for example propinyl, 2-butinyl, 3-butinyl, isobutinyl, n-2,4-pentadiinyl, 3-methyl-2-butinyl, n-2-octinyl, n-2-dodecinyl, isododecinyl.

Examples of alkoxy are methoxy, ethoxy, propoxy, isopropoxy, butoxy, isobutoxy, pentoxy, isopentoxy, hexoxy, heptoxy or octoxy.

C$_7$–C$_9$ phenylalkyl is for example benzyl, α-methylbenzyl, α,α-dimethylbenzyl or 2-phenylethyl, benzyl is preferred.

C$_5$–C$_{12}$cycloalkyl is for example cyclopentyl, cyclohexyl, cycloheptyl, methylcyclopentyl or cyclooctyl.

C$_5$–C$_{12}$cycloalkenyl is for example 3-cyclopentenyl, 3-cyclohexenyl or 3-cycloheptenyl.

If R$_1$ is a monovalent radical of a saturated, unsaturated or aromatic carboxylic acid, it is, for example, an acetyl, caproyl, stearoyl, acryloyl, methacryloyl, benzoyl or β-(3, 5-di-tert-butyl-4-hydroxyphenyl)propionyl radical.

If R$_1$ is a divalent radical of a dicarboxylic acid, it is, for example, a malonyl, succinyl, glutaryl, adipoyl, suberoyl, sebacoyl, maleoyl, itaconyl, phthaloyl, dibutylmalonyl, dibenzylmalonyl, butyl(3,5-di-tert-butyl-4-hydroxybenzyl)malonyl or bicycloheptenedicarbonyl radical.

If R$_1$ is a trivalent radical of a tricarboxylic acid, it is, for example, a trimellitoyl, citryl or nitrilotriacetyl radical.

If R$_1$ is a tetravalent radical of a tetracarboxylic acid, it is, for example, the tetravalent radical of butane-1,2,3,4-tetracarboxylic acid or of pyromellitic acid.

Preferably n is 1 or 2 and more preferably n is 1.
Preferably at least one of G$_1$, G$_2$, G$_3$ or G$_4$ is ethyl or propyl, in particular ethyl.

Preferably X is selected from the group consisting of
—CH$_2$-phenyl, CH$_3$CH-phenyl, (CH$_3$)$_2$C-phenyl, (C$_5$–C$_6$cycloalkyl)$_2$CCN, (CH$_3$)$_2$CCN,

—CH$_2$CH=CH$_2$, CH$_3$CH—CH=CH$_2$ (C$_1$–C$_8$alkyl)CR$_{20}$—C(O)-phenyl, (C$_1$–C$_8$)alkyl-CR$_{20}$—C(O)—(C$_1$–C$_8$)alkoxy, (C$_1$–C$_8$)alkyl-CR$_{20}$—C(O)—(C$_1$–C$_8$)alkyl, (C$_1$–C$_8$)alkyl-CR$_{20}$—C(O)—N-di(C$_1$–C$_8$)alkyl, (C$_1$–C$_8$)alkyl-CR$_{20}$—C(O)—NH(C$_1$–C$_8$)alkyl, (C$_1$–C$_8$)alkyl-CR$_{20}$—C(O)—NH$_2$,
wherein
R$_{20}$ is hydrogen or (C$_1$–C$_8$)alkyl.

Particularly preferred is when X is selected from the group consisting of
—CH$_2$-phenyl, CH$_3$CH-phenyl, (CH$_3$)$_2$C-phenyl, (C$_5$–C$_6$cycloalkyl)$_2$CCN, (CH$_3$)$_2$CCN,

—CH$_2$CH=CH$_2$, CH$_3$CH—CH=CH$_2$ (C$_1$–C$_4$alkyl)CR$_{20}$—C(O)-phenyl, (C$_1$–$_{C4}$)alkyl-CR$_{20}$—C(O)—(C$_1$–C$_4$)alkyl-CR$_{20}$—C(O)—(C$_1$–C$_4$)alkyl, (C$_1$–C$_4$)alkyl-CR$_{20}$—C(O)—N-di(C$_1$–C$_4$)alkyl, (C$_1$–C$_4$)alkyl-CR$_{20}$—C(O)—NH(C$_1$–C$_4$)alkyl, (C$_1$–C$_4$)alkyl-CR$_{20}$—C(O)—NH$_2$,
wherein $R_{20}$ is hydrogen or $(C_1-C_4)$alkyl.

The most preferred substituent is $CH_3$—CH-phenyl.

In a particularly preferred embodiment of the invention at least one of $G_1$, $G_2$, $G_3$ and $G_4$ is ethyl and the others are methyl and $G_5$ and $G_6$ are each independently of the other hydrogen or methyl.

Preferably Y is O.

A preferred group of compounds is, wherein $G_1$ and $G_3$ are methyl and $G_2$ and $G_4$ are ethyl, or $G_1$ and $G_2$ are methyl and $G_3$ and $G_4$ are ethyl;

$G_5$ and $G_6$ are each independently of the other hydrogen or methyl; and

Y is O;

n is 1

$R_1$ is H, straight or branched $C_1-C_{18}$alkyl or $C_3-C_{18}$alkenyl; $C_5-C_{12}$cycloalkyl or $C_5-C_{12}$cycloalkenyl;

phenyl, $C_7-C_9$phenylalkyl or naphthyl which may be unsubstituted or substituted by one or more $C_1-C_8$alkyl, halogen, OH, $C_1-C_8$alkoxy; or —C(O)—$C_1-C_{36}$alkyl, or an acyl moiety of α,β-unsaturated carboxylic acid having 3 to 5 carbon atoms or of an aromatic carboxylic acid having 7 to 15 carbon atoms; and;

X is selected from the group consisting of —$CH_2$-phenyl, $CH_3$CH-phenyl, $(CH_3)_2$C-phenyl, $(C_5-C_6$cycloalkyl$)_2$CCN, $(CH_3)_2$CCN,

—$CH_2CH=CH_2$, $CH_3CH$—$CH=CH_2$ $(C_1-C_4$alkyl$)$ $CR_{20}$—C(O)-phenyl, $(C_1-C_4)$alkyl-$CR_{20}$—C(O)—$(C_1-C_4)$alkyl-$CR_{20}$—C(O)—$(C_1-C_4)$alkyl, $(C_1-C_4)$alkyl-$CR_{20}$—C(O)—N-di$(C_1-C_4)$alkyl, $(C_1-C_4)$alkyl-$CR_{20}$—C(O)—NH$(C_1-C_4)$alkyl, $(C_1-C_4)$alkyl-$CR_{20}$—C(O)—$NH_2$, wherein $R_{20}$ is hydrogen or $(C_1-C_4)$alkyl.

Preferred individual compounds are:

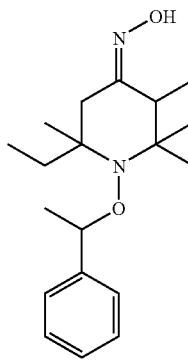

,

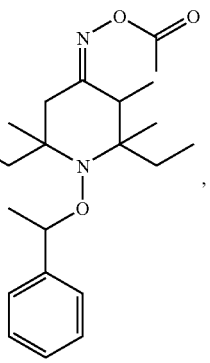

,

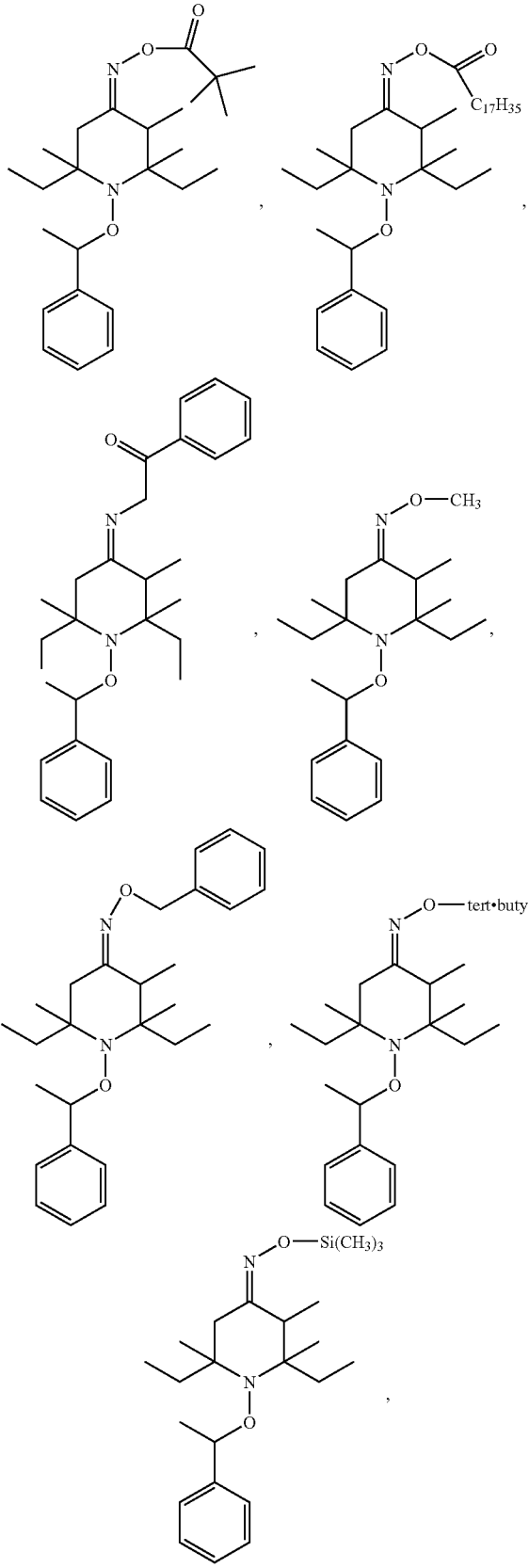

-continued

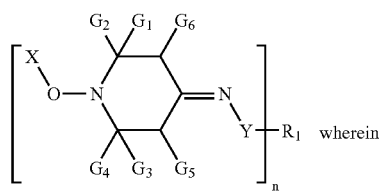
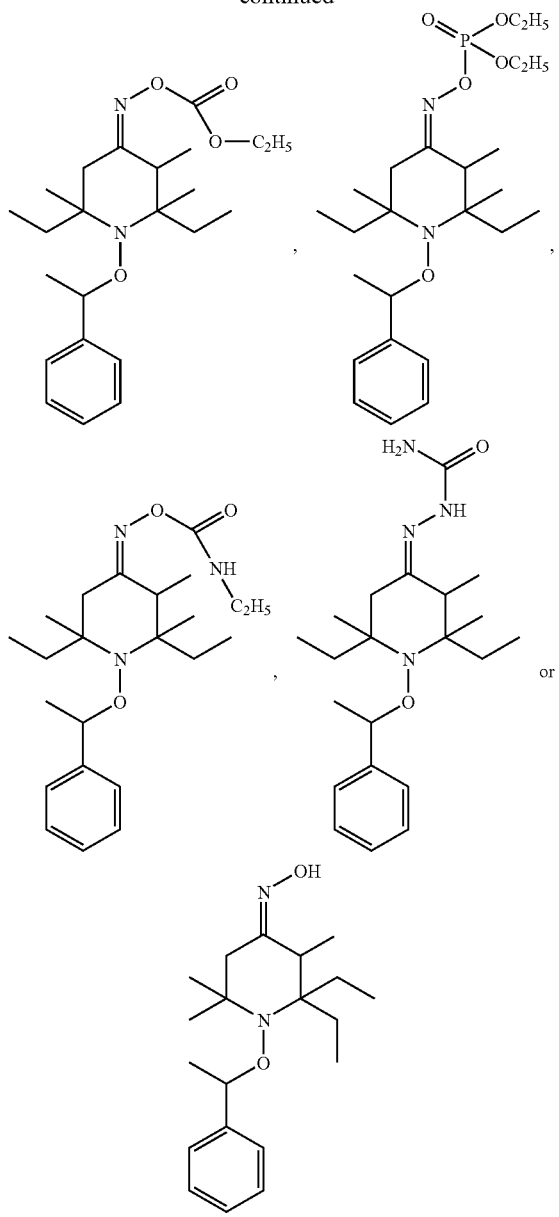

Particularly preferred are
a) 2,6-Diethyl-2,3,6-trimethyl-1-(1-phenyl-ethoxy)-piperidine-4-one oxime (compound 101, Table 1),
b) 2,6-Diethyl-2,3,6-trimethyl-1-(1-phenyl-ethoxy)-4-acetoximino-piperidine (compound 102, Table 1),
c) 2,2-Diethyl-6,6-dimethyl-1-(1-phenyl-ethoxy)-piperidine-4-one oxime (compound 104, Table 1),
d) 2,6-Diethyl-2,3,6-trimethyl-1-(1-phenyl-ethoxy)-4-pivaloyloximino-piperidine (compound 105, Table 1) or
e) 2,6-Diethyl-2,3,6-trimethyl-1-(1-phenyl-ethoxy)-4-benzoyloximino-piperidine (comjpound 106, Table 1).

A further subject of the invention is a polymerizable composition, comprising
a) at least one ethylenically unsaturated monomer or oligomer, and
b) a compound according to formula (I)

$$\left[ X-O-N \underset{G_4 \ G_3 \ G_5}{\overset{G_2 \ G_1 \ G_6}{\diagdown}} = N-Y \right]_n R_1 \quad \text{wherein} \tag{I}$$

$G_1$, $G_2$, $G_3$ and $G_4$ are independently $C_1$–$C_4$alkyl or $G_1$ and $G_2$ together and $G_3$and $G_4$ together, or $G_1$ and $G_2$ together or $G_3$ and $G_4$ together are pentamethylene;

$G_5$ and $G_6$ are each independently of the other hydrogen or $C_1$–$C_4$alkyl; and X represents a group such that the free radical X. derived from X is capable of initiating polymerization of ethylenically unsaturated monomers;

n is 1, 2, 3, or 4

Y is O NR$_2$ or when n is 1 and $R_1$ represents alkyl or aryl Y is additionally a direct bond;

$R_2$ is H, $C_1$–$C_{18}$alkyl or phenyl;

if n is 1

$R_1$ is H, straight or branched $C_1$–$C_{18}$alkyl, $C_3$–$C_{18}$alkenyl or $C_3$–$C_{18}$alkinyl, which may be unsubstituted or substitued, by one or more OH, $C_1$–$C_8$alkoxy, carboxy, $C_1$–$C_8$alkoxycarbonyl;

$C_5$–$C_{12}$cycloalkyl or $C_5$–$C_{12}$cycloalkenyl;

phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy, $C_1$–$C_8$alkoxycarbonyl;

—C(O)—$C_1$–$C_{36}$alkyl, or an acyl moiety of α,β-unsaturated carboxylic acid having 3 to 5 carbon atoms or of an aromatic carboxylic acid having 7 to 15 carbon atoms;

—SO$_3^-$Q$^+$, —PO(O$^-$Q$^+$)$_2$, —P(O)(OR$_2$)$_2$, —SO$_2$—R$_2$, —CO—NH—R$_2$, —CONH$_2$, COOR$_2$, or Si(Me)$_3$, wherein Q$^+$ is H$^+$, ammnonium or an alkali metal cation;

if n is 2

$R_1$ is $C_1$–$C_{18}$alkylene, $C_3$–$C_{18}$alkenylene or $C_3$–$C_{18}$alkinylene, which may be unsubstituted or substitued, by one or more OH, $C_1$–$C_8$alkoxy, carboxy, $C_1$–$C_8$alkoxycarbonyl;

or xylylene; or $R_1$ is a bisacyl radical of an aliphatic dicarboxylic acid having 2 to 36 carbon atoms, or a cycloaliphatic or aromatic dicarboxylic acid having 8–14 carbon atoms;

if n is3, $R_1$ is a trivalent radical of an aliphatic, cycloaliphatic or aromatic tricarboxylic acid; and if n is 4, $R_1$ is a tetravalent radical of an aliphatic, cycloaliphatic or aromatic tetracarboxylic acid.

Definitions and preferences for the individual substituents have already been given they apply also for the composition.

Preferably the initiator/regulator compound of formula (I) is present in an amount of from 0.01 mol-% to 20 mol-% more preferably in an amount of from 0.01 mol-% to 10 mol-% and most preferred in an amount of from 0.05 mol-% to 10 mol-% based on the monomer or monomer mixture.

When monomer mixtures are used mol-% is calculated on the average molecular weight of the mixture.

Preferably the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl)acrylic acid salts, (alkyl)acrylic esters, (meth)acrylonitriles, (alkyl)acrylamides, vinyl halides or vinylidene halides.

Particularly the ethylenically unsaturated monomers are ethylene, propylene, n-butylene, i-butylene, isoprene, 1,3-butadiene, $\alpha$-$C_5$–$C_{18}$alkene, styrene, $\alpha$-methyl styrene, p-methyl styrene or a compound of formula $CH_2$=$C(R_a)$—(C=Z)-$R_b$, wherein $R_a$ is hydrogen or $C_1$–$C_4$alkyl, $R_b$ is $NH_2$, $O^-(Me^+)$, glycidyl, unsubstituted $C_1$–$C_{18}$alkoxy, $C_2$–$C_{100}$alkoxy interrupted by at least one N and/or O atom, or hydroxy-substituted $C_1$–$C_{18}$alkoxy, unsubstituted $C_1$–$C_{18}$alkylamino, di($C_1$–$C_{18}$alkyl)amino, hydroxy-substituted $C_1$–$C_{18}$alkylamino or hydroxy-substituted di($C_1$–$C_{18}$alkyl)amino, —O—$CH_2$—$CH_2$—$N(CH_3)_2$ or —O—$CH_2$—$CH_2$—$N^+H(CH_3)_2$ $An^-$;

$An^-$ is a anion of a monovalent organic or inorganic acid;

Me is a monovalent metal atom or the ammonium ion.

Z is oxygen or sulfur.

Examples for $R_a$ as $C_2$–$C_{100}$alkoxy interrupted by at least one O atom are of formula

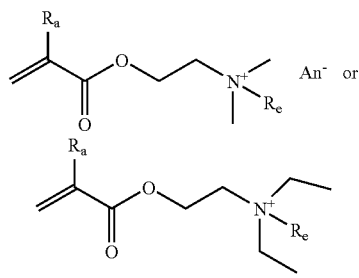

wherein $R_c$ is $C_1$–$C_{25}$alkyl, phenyl or phenyl substituted by $C_1$–$C_{18}$alkyl, $R_d$ is hydrogen or methyl and v is a number from 1 to 50. These monomers are for example derived from non ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

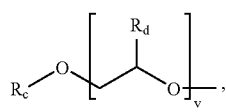

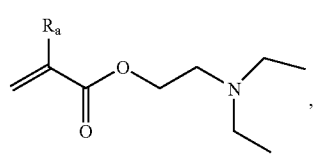

$An^-$, wherein $An^-$ and $R_a$ have the meaning as defined above and $R_e$ is methyl or benzyl. An is preferably $Cl^-$, $Br^-$ or $^-O_3S$—$CH_3$.

Further acrylate monomers are

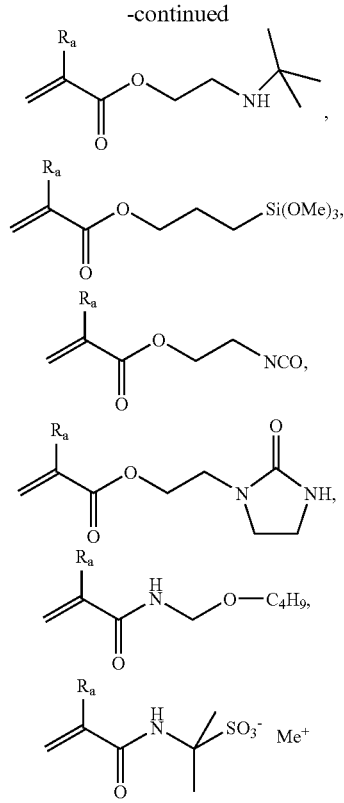

Examples for suitable monomers other than acrylates are

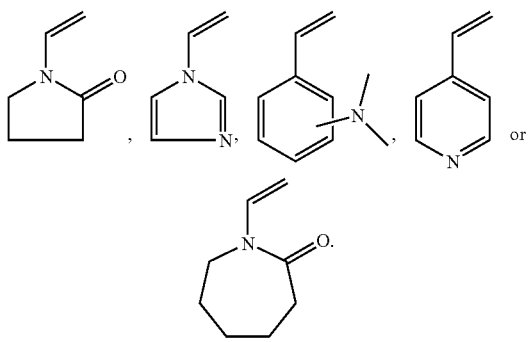

Preferably $R_a$ is hydrogen or methyl, $R_b$ is $NH_2$, gycidyl, unsubstituted or with hydroxy substituted $C_1$–$C_4$alkoxy, unsubstituted $C_1$–$C_4$alkylamino, di($C_1$–$C_4$alkyl)amino, hydroxy-substituted $C_1$–$C_4$alkylamino or hydroxy-substituted di($C_1$–$C_4$alkyl)amino;and Z is oxygen.

Particularly preferred ethylenically unsaturated monomers are styrene, methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl(meth)acrylate, ethyl(meth)acrylate, butyl(meth)acrylate, hydroxyethyl(meth)acrylate, hydroxypropyl(meth)acrylate, dimethylaminoethyl(meth) acrylate, glycidyl(meth)acrylates, acrylonitrile, acrylamide, methacrylamide or dimethylaminopropyl-methacrylamide.

A further subject of the invention is a process for preparing an oligomer, a cooligomer, a polymer or a copolymer (block or random) by free radical polymerization of at least one ethylenically unsaturated monomer or oligomer, which comprises (co)polymerizing the monomer or monomers/oligomers in the presence of an initiator compound of formula (I) under reaction conditions capable of effecting scission of the O—C bond to form two free radicals, the radical .X being capable of initiating polymerization.

Preferred is a process wherein the scission of the O—C bond is effected by ultrasonic treatment, heating or exposure to electromagnetic radiation, ranging from γ to microwaves.

More preferably the scission of the O—C bond is effected by heating and takes place at a temperature of between 50° C. and 160° C.

The process may be carried out in the presence of an organic solvent or in the presence of water or in mixtures of organic solvents and water. Additional cosolvents or surfactants, such as glycols or ammonium salts of fatty acids, may be present. Other suitable cosolvents are described hereinafter.

Preferred processes use as little solvents as possible. In the reaction mixture it is preferred to use more than 30% by weight of monomer and initiator, particularly preferably more than 50% and most preferrably more than 80%.

If organic solvents are used, suitable solvents or mixtures of solvents are typically pure alkanes (hexane, heptane, octane, isooctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), or mixtures thereof.

The aqueous polymerization reactions can be supplemented with a water-miscible or hydrophilic cosolvent to help ensure that the reaction mixture remains a homogeneous single phase throughout the monomer conversion. Any water-soluble or water-miscible cosolvent may be used, as long as the aqueous solvent medium is effective in providing a solvent system which prevents precipitation or phase separation of the reactants or polymer products until after all polymerization reactions have been completed. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof. When mixtures of water and water-soluble or water-miscible organic liquids are selected as the aqueous reaction media, the water to cosolvent weight ratio is typically in the range of about 100:0 to about 10:90.

The process is particularly useful for the preparation of block copolymers.

Block copolymers are, for example, block copolymers of polystyrene and polyacrylate (e.g., poly(styrene-co-acrylate) or poly(styrene-co-acrylate-co-styrene). They are usefull as adhesives or as compatibilizers for polymer blends or as polymer toughening agents. poly(methylmethacrylate-co-acrylate) diblock copolymers or poly(methylacrylate-co-acrylateco-methacrylate) triblock copolymers) are useful as dispersing agents for coating systeme, as coating additives (e.g. rheological agents, compatibilizers, reactive diluents) or as resin component in coatings(e.g. high solid paints) Block copolymers of styrene, (meth)acrylates and/or acrylonitrile are useful for plastics, elastomers and adhesives.

Furthermore, block copolymers of this invention, wherein the blocks alternate between polar monomers and non-polar monomers, are useful in many applications as amphiphilic surfactants or dispersants for preparing highly uniform polymer blends. The (co)polymers of the present invention may have a number average molecular weight from 1 000 to 400 000 g/mol, preferably from 2 000 to 250 000 g/mol and, more preferably, from 2 000 to 200 000 g/mol. When produced in bulk, the number average molecular weight may be up to 500 000 (with the same minimum weights as mentioned above). The number average molecular weight may be determined by size exclusion chromatography (SEC), gel permeation chromatography (GPC), matrix assisted laser desorptionrionization mass spectrometry (MALDI-MS) or, if the initiator carries a group which can be easily distinguished from the monomer(s), by NMR spectroscopy or other conventional methods.

The polymers or copolymers of the present invention have preferably a polydispersity of from 1.0 to 2, more preferably of from 1.1 to 1.9 and most preferably from 1.1 to 1.8.

Thus, the present invention also encompasses in the synthesis novel block, multi-block, star, gradient, random, hyperbranched and dendritic copolymers, as well as graft or copolymers.

The polymers prepared by the present invention are useful for following applications:

adhesives, detergents, dispersants, emulsifiers, surfactants, defoamers, adhesion promoters, corrosion inhibitors, viscosity improvers, lubricants, rheology modifiers, thickeners, crosslinkers, paper treatment, water treatment, electronic materials, paints, coatings, photography, ink materials, imaging materials, superabsorbants, cosmetics, hair products, preservatives, biocide materials or modifiers for asphalt, leather, textiles, ceramics and wood.

Because the present polymerizaton is a "living" polymerization, it can be started and stopped practically at will. Furthermore, the polymer product retains the functional alkoxyamine group allowing a continuation of the polymerization in a living matter. Thus, in one embodiment of this invention, once the first monomer is consumed in the initial polymerizing step a second monomer can then be added to form a second block on the growing polymer chain in a second polymerization step. Therefore it is possible to carry out additional polymerizations with the same or different monomer(s) to prepare multi-block copolymers.

Furthermore, since this is a radical polymerization, blocks can be prepared in essentially any order. One is not necessarily restricted to preparing block copolymers where the sequential polymerizing steps must flow from the least stabilized polymer intermediate to the most stabilized polymer intermediate, such as is the case in ionic polymerization. Thus it is possible to prepare a multi-block copolymer in which a polyacrylonitrile or a poly(meth)acrylate block is prepared first, then a styrene or butadiene block is attached thereto, and so on.

Furthermore, there is no linking group required for joining the different blocks of the present block copolymer. One can simply add successive monomers to form successive blocks.

A plurality of specifically designed polymers and copolymers are accessible by the present invention, such as star and graft (co)polymers as described, inter alia, by C. J. Hawker in Angew. Chemie, 1995, 107, pages 1623–1627, dendrimers as described by K. Matyaszewski et al. in Macrmolecules 1996, Vol 29, No. 12, pages 4167–4171, graft (co)polymers as described by C. J. Hawker et al. in Macromol. Chem. Phys. 198, 155–166(1997), random copolymers as described by C. J. Hawker in Macromolecules 1996, 29, 2686–2688, or diblock and triblock copolymers as described by N. A. Listigovers in Macromolecules 1996, 29, 8992–8993.

Also subject of the invention is a compound of formula (II)

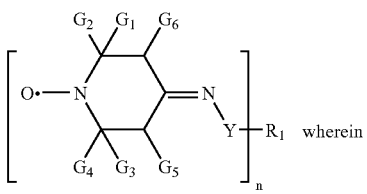

wherein
$G_1$ and $G_3$ are independently $C_1$–$C_4$alkyl;
$G_2$ and $G_4$ are independently $C_2$–$C_4$alkyl;
$G_5$ and $G_6$ are each independently of the other hydrogen or $C_1$–$C_4$alkyl;
n is 1, 2, 3, or 4
Y is O, $NR_2$ or when n is 1 and $R_1$ represents alkyl or aryl Y is additionally a direct bond;
$R_2$ is H, $C_1$–$C_{18}$alkyl or phenyl;
if n is 1
$R_1$ is H, straight or branched $C_1$–$C_{18}$alkyl, $C_3$–$C_{18}$alkenyl or $C_3$–$C_{18}$alkinyl, which may be unsubstituted or substitued, by one or more OH, $C_1$–$C_8$alkoxy, carboxy, $C_1$–$C_8$alkoxycarbonyl;
$C_5$–$C_{12}$cycloalkyl or $C_5$–$C_{12}$cycloalkenyl;
phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy, $C_1$–$C_8$alkoxycarbonyl;
—C(O)—$C_1$–$C_{36}$alkyl, or an acyl moiety of a α,β-unsaturated carboxylic acid having 3 to 5 carbon atoms or of an aromatic carboxylic acid having 7 to 15 carbon atoms;
—$SO_3^-Q^+$, —$PO(O^-Q^+)_2$, —$P(O)(OR_2)_2$, —$SO_2$—$R_2$, —CO—NH—$R_2$, —$CONH_2$, $COOR_2$, or $Si(Me)_3$, wherein $Q^+$ is $H^+$, ammnonium or an alkali metal cation;
if n is 2
$R_1$ is $C_1$–$C_{18}$alkylene, $C_3$–$C_{18}$alkenylene or $C_3$–$C_{18}$alkinylene, which may be unsubstituted or substituted, by one or more OH, $C_1$–$C_8$alkoxy, carboxy, $C_1$–$C_8$alkoxycarbonyl;
or xylylene; or
$R_1$ is a bisacyl radical of an aliphatic dicarboxylic acid having 2 to 36 carbon atoms, or a cycloaliphatic or aromatic dicarboxylic acid having 8–14 carbon atoms;
if n is 3,
$R_1$ is a trivalent radical of an aliphatic, cycloaliphatic or aromatic tricarboxylic acid; and
if n is 4, $R_1$ is a tetravalent radical of an aliphatic, cycloaliphatic or aromatic tetracarboxylic acid.

Definitions and preferences for the individual substituents have already been given and apply also for the compounds of formula (II).

Consequently a further subject of the invention is a polymerizable composition, comprising
a) at least one ethylenically unsaturated monomer or oligomer, and
b) a compound according to formula (II)

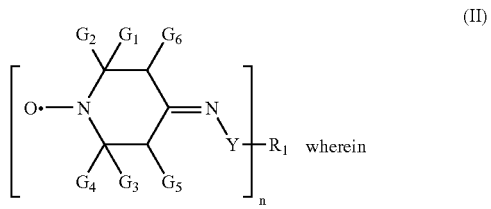

$G_1$, $G_2$, $G_3$ and $G_4$ are independently $C_1$–$C_4$alkyl or $G_1$ and $G_2$ together and $G_3$ and $G_4$ together, or $G_1$ and $G_2$ together or $G_3$ and $G_4$ together are pentamethylene;
$G_5$ and $G_6$ are each independently of the other hydrogen or $C_1$–$C_4$alkyl;
n is 1, 2, 3, or 4
Y is O, $NR_2$ or when n is 1 and $R_1$ represents alkyl or aryl Y is additionally a direct bond;
$R_2$ is H, $C_1$–$C_{18}$alkyl or phenyl;
if n is 1
$R_1$ is H, straight or branched $C_1$–$C_{18}$alkyl, $C_3$–$C_{18}$alkenyl or $C_3$–$C_{18}$alkinyl, which may be unsubstituted or substitued, by one or more OH, $C_1$–$C_8$alkoxy, carboxy, $C_1$–$C_8$alkoxycarbonyl;
$C_5$–$C_{12}$cycloalkyl or $C_5$–$C_{12}$cycloalkenyl;
phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy, $C_1$–$C_8$alkoxycarbonyl;
—C(O)—$C_1$–$C_{36}$alkyl, or an acyl moiety of a α,β-unsaturated carboxylic acid having 3 to 5 carbon atoms or of an aromatic carboxylic acid having 7 to 15 carbon atoms;
—$SO_3^-Q^+$, —$PO(O^-Q^+)_2$, —$P(O)(OR_2)_2$, —$SO_2$—$R_2$, —CO—NH—$R_2$, —$CONH_2$, $COOR_2$, or $Si(Me)_3$, wherein $Q^+$ is $H^+$, ammnonium or an alkali metal cation;
if n is 2
$R_1$ is $C_1$–$C_{18}$alkylene, $C_3$–$C_{18}$alkenylene or $C_3$–$C_{18}$alkinylene, which may be unsubstituted or substituted, by one or more OH, $C_1$–$C_8$alkoxy, carboxy, $C_1$–$C_8$alkoxycarbonyl;
or xylylene; or
$R_1$ is a bisacyl radical of an aliphatic dicarboxylic acid having 2 to 36 carbon atoms, or a cycloaliphatic or aromatic dicarboxylic acid having 8–14 carbon atoms;
if n is 3,
$R_1$ is a trivalent radical of an aliphatic, cycloaliphatic or aromatic tricarboxylic acid; and
if n is 4, $R_1$ is a tetravalent radical of an aliphatic, cycloaliphatic or aromatic tetracarboxylic acid; and
c) a source of free radicals.

The source of radicals may be a bis-azo compound, a peroxide, a perester or a hydroperoxide.

The production of C-centered radicals is described, inter alia, in Houben Weyl, Methoden der Organischen Chemie, Vol. E 19a, pages 60–147. These methods can be applied in general analogy.

Preferably, the source of radicals is 2,2'-azobisisobutyronitrile, 2,2'-azobis(2-methylbutyronitrile), 2,2'-azobis(2,4-dimethylvaleronitrile), 2,2'-azobis(4-methoxy-2,4-dimethylvaleronitrile), 1,1'-azobis(1-cyclohexanecarbonitrile), 2,2'-azobis(isobutyramide) dihydrate, 2-phenylazo-2,4-dimethyl-4-methoxyvaleronitrile, dimethyl-2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine), free base or hydrochloride, 2,2'-azobis(2-amidinopropane), free base or hydrochloride, 2,2'-azobis{2-methyl-N-[1,1bis(hydroxymethyl)ethyl]propionamide} or 2,2'-azobis{2-methyl-N-[1,1-bis(hydroxymethyl)-2-hydroxyethyl]propionamide.

Preferred peroxides and hydroperoxides are acetyl cyclohexane sulphonyl peroxide, diisopropyl peroxy dicarbonate, t-amyl pemeodecanoate, t-butyl pemeodecanoate, t-butyl perpivalate, t-amylperpivalate, bis(2,4-dichlorobenzoyl)peroxide, diisononanoyl peroxide, didecanoyl peroxide, dioctanoyl peroxide, dilauroyl peroxide, bis (2-methylbenzoyl) peroxide, disuccinic acid peroxide, diacetyl peroxide, dibenzoyl peroxide, t-butyl per 2-ethylhexanoate, bis-(4-chlorobenzoyl)-peroxide, t-butyl perisobutyrate, t-butyl permaleinate, 1,1-bis(t-butylperoxy)3,5,5-trimethylcyclohexane, 1,1-bis(t-butylperoxy)cyclohexane, t-butyl peroxy isopropyl carbonate, t-butyl perisononaoate, 2,5-dimethylhexane 2,5-dibenzoate, t-butyl peracetate, t-amyl perbenzoate, t-butyl perbenzoate, 2,2-bis (t-butylperoxy) butane, 2,2 bis(t-butylperoxy)propane, dicumyl peroxide, 2,5-dimethylhexane-2,5-di-t-butylperoxide, 3-t-butylperoxy 3phenylphthalide, di-t-amyl peroxide, α,α'-bis(t-butylperoxy isopropyl)benzene, 3,5-bis(t-butylperoxy)-3,5-dimethyl 1,2-dioxolane, di-t-butyl peroxide, 2,5-dimethylhexyne-2,5-di-t-butylperoxide, 3,3,6,6,9,9-hexamethyl 1,2,4,5-tetraoxa cyclononane, p-menthane hydroperoxide, pinane hydroperoxide, diisopropylbenzene mono-α-hydroperoxide, cumene hydroperoxide or t-butyl hydroperoxide.

These compounds are commercially available.

If more than one radical source is used, a mixture of substitution patterns is obtainable.

Preferably the compound of formula (II) is present in an amount of from 0.01 mol-% to 20 mol-% , based on the monomer or monomer mixture, more preferably of from 0.01 mol-% to 10 mol-% and most preferably of from 0.05 mol-% to 10 mol-%.

The radical source is preferably present in an amount of from 0.01 mol-% to 20 mol-%, more preferred in an amount of from 0.01 mol-% to 10 mol-% and most preferred in an amount of from 0.05 mol-% to 10 mol-% based on the monomer or monomer mixture.

The molar ratio of the radical source to the compound of formula II may be from 1:10 to 10:1, preferably from 1:5 to 5:1 and more preferably from 1:2 to 2:1.

Also subject of the invention is a process for preparing an oligomer, a cooligomer, a polymer or a copolymer (block or random) by free radical polymerization of at least one ethylenically unsaturated monomer or oligomer, which comprises (co)polymerizing the monomer or monomers/oligomers in the presence of a compound of formula (II) and a source of free radicals the radical being capable of initiating polymerization.

Definitions and preferences as well as reaction conditions have already been given and apply also for the process.

Yet further subjects of the invention are a polymer prepared by radical polymerization according to one of the above mentioned processes having attached a group of formula (III)

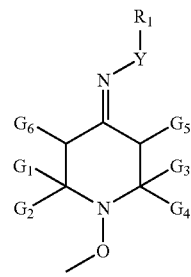

wherein the substituents are as defined above; and the use of a compound of formula (I) or of a compound of formula (II) together with a source of free radicals for the controlled radical (co)polymerization of ethylenically unsaturated monomers.

The compounds of formula II can be prepared for example according to E. G. Rozantsev, A. V. Chudinov, V. D. Sholle.: Izv. Akad. Nauk. SSSR, Ser. Khim. (9), 2114 (1980), starting from the corresponding 4-oxonitroxide in a condensation reaction with hydroxylamine and subsequent reaction of the OH group.

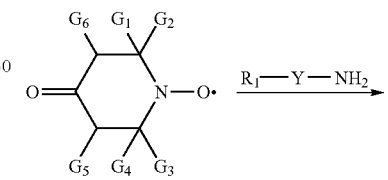

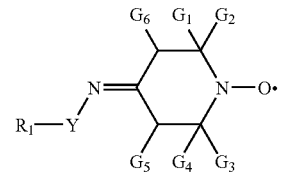

Another possible reaction scheme is to first react the 4-oxonitroxide with an amine or hydrazine to yield the corresponding imine as for example described in FR 1503149.

It is, however also possible to firstly react the 4-oxopiperidine with hydroxylamine, hydrazine or with a semicarbacide to the corresponding imino-compound and oxidising the imino piperidine to the corresponding nitroxide.

The alkoxyamines of formula I may be prepared from the corresponding nitroxides as for example described in GB 2335190.

A particularly suitable process for the preparation of the compounds of formula (I) starts from the 4-oxoalkoxyamines, the preparation of which is also described in GB 2335190:

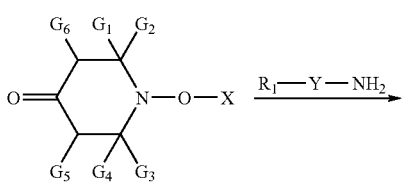

-continued

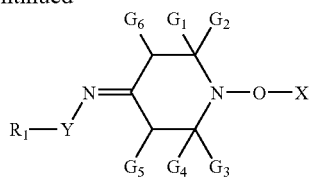

Since the 4-oxo-alkoxyamines already may have several asymmetrical carbon atoms, a variety of stereo isomers is usually obtained as mixture with different ratios of the individual isomers. It is however possible to separate the individual isomers in pure form. Mixtures of the stereo isomers as well as the pure individual isomers are within the scope of the present invention.

The ratio of the stereo isomers can be influenced by suitable catalysts such as bases or acids. This isomer equilibration can be done at the stage of the 4-oxo-alkoxyamine, during the imine forming reaction or at the stage of the final 4-imino-alkoxyamine. The shifting of the stereo isomer ratio allows to increase the overall yield, achievable for example by crystallisation.

Suitable bases are for example alkali metal or alkaline earth metal hydroxides or alcoholates such as LiOH, KOH, NaOH or Ca(OH)$_2$, NaOCH$_3$, NaOCH$_2$CH$_3$, Mg-ethanolate or K-tert. butylate. Also suitable bases are amines, particularly secondary or tertiary amines, such as piperidine, morpholine, pyridine, triethylamine or amidines such as DBU (diazabicycloundecane), DABCO (diazabicyclooctane).

Suitable acids are for example strong mineral acids, such as HCl, H$_2$SO$_4$, H$_3$po$_4$ organic sulfonic acids, such as CH$_3$SO$_3$H or para-toluene sulfonic acid, trichloro acetic acid or trifluoro acetic acid, organic acids, such as formic acid, acetic acid or benzoic acid, Lewis acids, such as AlCl$_3$ or BF$_3$, complex acids, such as HBF$_4$ or HPF$_6$.

A further aspect of the instant invention is an improved process for the preparation of a compound of formula (I)

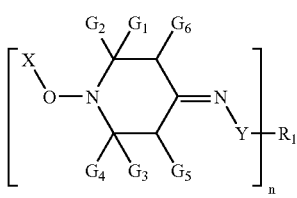

(I) comprising reacting a compound of formula (X)

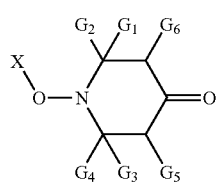

(X) with a compound of formula (XI) R$_1$—Y—NH$_2$ (XI) wherein the substituents have the meaning as defined above, characterized in that the compound of formula (X) is firstly treated with an acid or base catalyst or the acid or base catalyst is added during the imine forming reaction.

The imine forming reaction from a ketone and a substituted amine is known per se.

Suitable acid or base catalysts have already been mentioned. They are preferably used in a concentration of from 0.01 to 10%, more preferably of from 0.1 to 10% and most preferably of from 1 to 5% by weight based on the educt.

If the compound of formula (X) is pretreated with the catalyst the treatment duration is typically of from 1 minute to 10 hours, more preferably from 10 minutes to two hours.

The treatment may be preferably done at room temperature, however, it is also possible to work at 0° C. up to 150° C.

It can be done in solution or in bulk. Typical solvents are alcohols, ethers, esters, ketones aliphatic or aromatic hydrocarbons.

The pretreated compound of formula (X) can be subjected to the imine forming reaction immediately or after storage. The catalyst can be removed or left in the reaction mixture.

When the acid or base catalyst is added during the reaction, it is preferably added at the beginning. It is, however, possible to add the catalyst at a later stage.

The following examples illustrate the invention.

A) PREPARATION EXAMPLES

Example A1

2,6-Diethyl-2,3,6-trimethyl-1-(1-phenyl-ethoxy)-piperidine-4-one oxime (Table 1, Comp. 101)

2,6-diethyl-2,3,6-trimethyl-1-(1-phenyl-ethoxy)-4-oxopiperidine prepared according to DE 199 09 767 A1 is dissolved in methanol containing 10% by weight of KOH and stirred for 5 hours at room temperature. Methanol is evaporated, the residue is washed with water and dried in vacuo. A solution of 95.24 g (0.3 mol) of 2,6-diethyl-2,3,6-trimethyl-1-(1-phenyl-ethoxy)-4-oxopiperidine and 29.7 g (0.45 mol) 50% aqueous hydroxylamine solution in 150 ml of methanol is stirred under reflux during 5 h. The suspension is then cooled to –8° C. and filtered. The solid is washed with 100 ml of a cold (–20° C.) methanol and dried to afford 64 g (64.1%) of the title compound as a white, microcrystalline powder, mp 130–145° C. C$_{20}$H$_{32}$N$_2$O$_2$ (332.49) calculated C, 72.25%; H, 9.70%; N, 8.43%. found 72.19% C; 9.54% H; 8.43 % N.

Example A2

2,6-Diethyl-2,3,6-trimethyl-1-(1-phenyl-ethoxy)-4-acetoximino-piperidine (Table 1, Comp. 102)

To a suspension of 10 g (0.03 mol) 2,6-diethyl-2,3,6-trimethyl-1-(1-phenyl-ethoxy)piperidine-4-one oxime in 20 ml ethylacetate are added 0.1 g 4-dimethylamino-pyridin and 3.8 ml (0.04 mol) acetanhydride. The mixture is then stirred 2 h at room temperature. The homogeneous clear solution formed during this period is washed with water and NaHCO$_3$ solution and evaporated under vacuo to afford 11.2 g (99.7%) of the title compound as a colorless oil.

$^1$H-NMR (300 HMz, CDCl$_3$): 7.33–7.20 m (5ArH), 4.81–4.72 m (1H), 3.3–0.62 m (22H), 2.15 s (OC—CH$_3$), 1.45 d (CH$_3$).

Example A3

2,6-Diethyl-2,3,6-trimethyl-1-(1-phenyl-ethoxy)-piperidine-4-one semicarbazone (Table 1, Comp. 103)

2,6-diethyl-2,3,6-trimethyl-1-(1-phenyl-ethoxy)-4-oxopiperidine prepared according to DE 199 09 767 A1 is dissolved in methanol containing 10% by weight of KOH and stirred for 5 hours at room temperature. Methanol is evaporated, the residue is washed with water and dried in vacuo. To a solution of 6.4 g (0.02 mol) 2,6-diethyl-2,3,6-trimethyl-1-(1-pheyl-ethoxy)-piperidine-4-one in 20 ml methanol are added 3.3 g (0.03 mol) semicarbazide hydrochloride and 1.67 g (0.025 mol) KOH (85%). The mixture is stirred under reflux 5 h and then diluted with 200 ml water. The precipitate is extracted into 100 ml of dichloromethane, the organic layer is washed with water, dryied over MgSO4 and evaporated to give 7.8 g (98.8%) of the title compound as a slightly yellow resin.

$^1$H-NMR (300 HMz, CDCl$_3$): 8.5–7.7 bm (1H), 7.39–7.16 m (5 ArH), 6.5–5.0 bm (2H), 4.87–4.64 m (1 H), 2.7–0.63 m (25H)

Example A4

2,2-Diethyl-6,6-dimethyl-1-(1-phenyl-ethoxy)-piperidineone-4-one oxime (Table 1, Comp. 104)

2,2-diethyl-6,6-dimethyl-piperidine-4-one (preparation see Monatshefte für Chemie 88, 464 (1957)) is converted into the corresponding nitroxide which is further transformed into 2,2-diethyl-6,6-dimethyl-1-(1-phenyl-ethoxy)-piperidine-4-one using the methodology described in DE 199 09 767 A1. Colorless oil, $^1$H-NMR (300 HMz, CDCl$_3$): 7.34–7.23 m (5 ArH), 4.80–4.73 m (1H), 2.6–0.64 m (20H), 1.49 d (CH$_3$). This alkoxyamine (6.06 g, 0.02 mol) is then, in analogy to example 1, reacted with 1.77 ml (0.03 mol) of 50% aqueous hydroxylamine in 10 ml methanol. The title compound (5.15 g, 81%) is obtained after chromatography on silica gel with hexane-ethylacetate (4:1) as a colorless oil.

$^1$H-NMR (300 HMz, CDCl$_3$): 8.5 bs (1H), 7.36–7.21 m (5ArH), 4.78–4.70 m (1H), 3.1–0.64 m (20H), 1.52 d (CH$_3$).

Example A5

2,6-Diethyl-2,3,6-trimethyl-1-(1-phenyl-ethoxy)-4-pivaloyloximino-piperidine (Table 1, Comp. 105)

To a suspension of 10 g (0.03 mol) 2,6-diethyl-2,3,6-trimethyl-1-(1-phenyl-ethoxy)-piperidine-4-one oxime in 70 ml toluene are added 4.6 ml (0.033 mol) triethylamine and therafter dropwise 4 g (0.033 mol) pivaloylchlorid. The mixture is then stirred 17 h at rt. The precipitated Et$_3$N.HCl is filtered off, the filtrate is washed with 2×50 ml 5% NaOH, dried over MgSO$_4$ and evaporated in vacuo. The residue is chromatographed on silica gel with hexane-ethylacetate (9:1) to afford 12.1 g (96.8%) of the title compound as a colorless oil.

$^1$H-NMR (300 HMz, CDCl$_3$): 7.34–7.20 m (5ArH), 4.81–4.73 m (1H), 3.3–0.62 m (22H), 1.45 d (CH$_3$), 1.30 bs (9H, t-Bu).

Example A6

2,6-Diethyl-2,3,6-trimethyl-1-(1-phenyl-ethoxy)-4-benzoyloximino-pineridine (Table 1, Comp. 106)

From 10 g (0.03 mol) 2,6-diethyl-2,3,6-trimethyl-1-(1-phenyl-ethoxy)-piperidine-4-one oxime, 4.65 g (0.033 mol) benzoylchloride and 4.6 ml (0.033 mol) triethylamine are prepared in analogy to example A5. 8.1 g (61.8%) of the title compound is obtained as a colorless solid after treating with methanol, mp. 78–125° C. (mixture of isomers).

$^1$H-NMR (300 HMz, CDCl$_3$): 8.05–8.0 (m, 2ArH), 7.59–7.54 m (1ArH), 7.50–7.42 m (2ArH), 7.31–6.91 m (5ArH), 4.83–4.75 m (1H), 3.3–0.62 m (22H), 1.47 d (CH$_3$).

Example A7

2,6-Diethyl-2,3,6-trimethyl-1-(1-phenyl-ethoxy)-4-N-ethylcarbamoyl-oximino-piperidine (Table 1, Comp. 107)

To a suspension of 10 g (0.03 mol) 2,6-diethyl-2,3,6-trimethyl-1-(1-phenyl-ethoxy)-piperidine-4-one oxime in 50 ml toluene are added 2.6 ml (0.033 mol) ethylisocyanate. The mixture is stirred 3 h at rt and thereafter heated for another 3 h at 35° C., then filtered and evaporated under reduced pressure to afford 12.1 g (99.2%) of the title compound as a colorless oil.

$^1$H-NMR (300 HMz, CDCl$_3$): 7.33–7.12 m (5ArH), 6.36–6.30 bs (NH), 4.80–4.71 m (1H), 3.39–3.30 (q, CH$_2$), 3.25–0.62 m (25H), 1.45 d (CH$_3$).

Example A8

2,6-Diethyl-2,3,6-trimethyl-1-(1-phenyl-ethoxy)-4-stearoyloximino-piperidine (Table 1, Comp. 108)

10 g (0.03 mol) 2,6-diethyl-2,3,6-trimethyl-1-(1-phenyl-ethoxy)-piperidine-4-one oxime, 9.7 9 (0.032 mol) stearoylchloride and 4.6 ml (0.033 mol) triethylamine are reacted in analogy to example A5. 16.65 g (92.7%) of the title compound is obtained as a colorless oil after chromatography on silica gel with hexane-ethylacetate (10:1).

$^1$H-NMR (300 HMz, CDCl$_3$): 7.33–7.20 m (5ArH), 4.78–4.74 m (1H), 3.20–0.62 m (57H), 1.45 d (CH$_3$).

Example A9

2,6-Diethyl-2,3,6-trimethyl-1-(1-phenyl-ethoxy)-4-methoximino-piperidine (Table 1, Comp. 109)

To a suspension of 12 g (0.036 mol) 2,6-diethyl-2,3,6-trimethyl-1-(1-phenyl-ethoxy)-piperidine-4-one oxime in 40 ml dimethylformamide is added under nitrogen 1.75 g (0.0397 mol) sodium hydride (55% in mineral oil) and the mixture is stirred at 35° C. for 2 h. To the slightly turbid, yellow solution is then dropwise added at 10–20° C. 5.65 g (0.0397 mol) methyl iodide. The mixture is diluted after 18 h stirring at room temperature with 200 ml cold water and extracted with 2×100 ml hexane. The extracts are dried over MgSO4 and evaporated under reduced pressure. Chromatography of the residue on silica gel with hexane-ethyl acetate (24:1) afforded 9.6 g (77%) of the title compound as a colorless oil.

$^1$H-NMR (300 HMz, CDCl$_3$): 7.32–7.19 m (5ArH), 4.80–4.72 m (1H), 3.82 (s, CH$_3$O), 3.25–0.62 m (22H), 1.45 d (CH$_3$).

Example A10

1-Benzyloxy-2,6-diethyl-2,3,6-trimethyl-piperidine-4-one-O-benzyloxime (Table 1, Comp. 110)

a) A solution of 20 g (96.8 mmol) 2,6-diethyl-2,3,6-trimethyl-piperidine-4-one oxime-1-oxyl in 200 ml petroleum ether (40–60° C.) was under nitrogen 17 h vigorously stirred with a solution of 80 g of sodium ascorbate in 100 ml water. The slurry was cooled to 10° C., filtered, the precipitate was washed with water and hexane and dried in vacuo to give 19.95 g of a white 2,6-diethyl-2,3,6-trimethyl-1-hydroxy-piperidineone-4-one.

b) To a slurry of 3.8 g (87.5 mmol) sodium hydride (55% in mineral oil) in 40 ml DMFA were added 8 g (35 mmol) 2,6-diethyl-2,3,6-trimethyl-1-hydroxy-piperidine-4one. The mixture was stirred for 1 h at 30° C. and then cooled to 5° C. Thereafter, 10.4 ml (87.5 mmol) benzyl bromide were added dropwise at 5–10° C. The mixture was stirred for additional 3 h, then poured into 200 ml of cold water and extracted with 2×50 ml methyl-t-butyl ether. The extracts were evaporated and chromatographed on silica gel with hexane-ethylacetate (39:1) to give 10.8 g (75.5%) of the title compound as a colorles oil.

$^1$H-NMR (300 MHz, CDCl$_3$): 7.5–7.2 m (10 ArH), 5.1–5.04 m (2H), 4.9–4.7 m (2 H), 3.4–0.7 (m, 22H).

Example A11

1-Allyloxy-2,6-diethyl-2,3,6-trimethyl-piperidine-4-one-O-allyl-oxime (Table 1, Comp. 111)

To a slurry of 5.2 g (120 mmol) sodium hydride (55% in mineral oil) in 50 ml DMFA were added 9.6 g (42 mmol) 2,6-diethyl-2,3,6-trimethyl-1-hydroxy-piperidine-4-one. The mixture was stirred for 75 minutes at 30° C. and then cooled to room temperature. Thereafter, 14.5 g (120 mmol) allyl bromide were added dropwise at room temperature. The mixture was stirred for additional 2 h, then poured into 200 ml of cold water and extracted with 3×50 ml hexane. The extracts were evaporated and chromatographed on silica gel with hexane-ethylacetate (39:1) to give 10.75 g (83%) of the title compound as a colorles oil.

For C$_{18}$H$_{32}$N$_2$O$_2$ calculated: C, 70.09%; H, 10.46%; N, 9.08%. found C, 70.03; H, 11.23%; N, 9.14%.

Example A12

2,6-Diethyl-2,3,6-trimethyl-1-(1-phenyl-ethoxy)-piperidine-4-one-O-diethylphosphonato-oxime (Table 1, Comp. 112)

To a stirred suspension of 10 g (30 mmol) 2,6-diethyl-2,3,6-trimethyl-1-(1-phenyl-ethoxy)-piperidine-4-one oxime in 70 ml toluene are added 4.6 ml (33 mmol) of triethylamine, 5.7 ml (33 mmol) of diethylchlorophosphate and 0.15 g of 4-dimethylaminopyridine. The mixture is stirred for 72 h at room temperature, and heated therafter for additional 24 h at 60° C. It is then cooled to room temperature, washed 2× with 50 ml water, dried over MgSO$_4$ and evaporated. The residue is chromatographed on silica gel with hexane-ethyl acetate (2:1) to give 9.3 g (66%) of the title compound as a colorless oil.

$^1$H-NMR (300 MHz, CDCl$_3$): 7.33–7.22 m(5H), 4.79–4.74 m (1H), 4.26–4.16 m(4H), 3.5–0.5 m (31H).
$^{31}$p-NMR (162 MHz, CDCl$_3$): 1.655–1.355 m

Example A13

[2,6-Diethyl-2,3,6-trimethyl-1-(1-phenyl-ethoxy)-piperidine-4-ylideneaminooxy]-acetic acid-teroom temperature.-butyl ester (Table 1, Comp. 113)

To a suspension of 16.62 g (50 mmol) 2,6-diethyl-2,3,6-trimethyl-1-(1-phenyl-ethoxy)-piperidine-4-one oxime in 70 ml dry DMFA were added 2.4 g (55 mmol) sodium hydride (55% in mineral oil). The mixture was stirred at 40° C. for 1 hour and cooled to 10° C. Thereafter, 8.1 ml (55 mmol) of t-butyl-bromoacetate were added dropwise and the mixture was stirred at room temperature for 18 hours. It was then diluted with 300 ml water and extracted twice with 100 ml of methyl-t-butyl ether. The extracts were washed 3 times with 50 ml water, dried over MgSO$_4$ and evaporated. The residue was chromatographed on silica gel with hexane-ethyl acetate (19:1) to give 20.85 g (93.5%) of the title compound as a colorless oil.

$^1$H-NMR (300 MHz, CDCl$_3$): 7.33–7.19 m (5 H), 4.81–4.73 m (1H), 4.47–4.45 m (2H), 3.1–0.5 m (25 H), 1.46 s (9H)

Example A14

[2,6-Diethyl-2,3,6-trimethyl-1-(1-phenyl-ethoxy)-piperidine-4-ylideneaminooxy]-acetic acid (Table 1, Comp. 114)

In 30 ml of trifluoroacetic acid were dissolved 10.1 g (22.6 mmol) of [2,6-diethyl-2,3,6-trimethyl-1-(1-phenyl-ethoxy)-piperidine-4-ylideneaminooxy]-acetic acid-teroom temperature.-butyl ester and the clear solution was stirred under nitrogen at room temperature for 4 hours. The mixture was then diluted with 300 ml water and extracted with 2×50 ml of methyl-t-butyl ether. The extracts were washed 3 times with 50 ml water, evaporated and chromatographed on silica gel with hexane-ethylacetate 2:1 to give 4.7 g (53%) of the title compound as a colorless oil.

$^1$H-NMR (300 MHz, CDCl$_3$): 7.37–7.20 m (5 H), 4.80–4.72 m (1 H), 4.62–4.60 m (2H), 3.4–0.5 m (26H).

Example A15

2,2,6,6-Tetramethyl-1-(1-phenyl-ethoxy)-piperidine-4-one oxime (Table 1, Comp. 115)

To a solution of 36 g (130 mmol) of 2,2,6,6-tetramethyl-1-(1-phenyl-ethoxy)-piperidine-4-one (prepared as described in Eur. Pat. Appl. (1990), E 389430 A1) in 50 ml of methanol were added 26 g (390 mmol) of 50% aqueous hydroxylamine. The mixture was refluxed for 90 minutes and then evaporated. The residue was chromatographed on 450 g of silica gel with hexane-ethyl acetate (4:1) to give 21.05 g (55%) of the title compound as a colorless oil, slowly solidifying on standing.

$^1$H-NMR (300 MHz, CDCl$_3$): 8.9 bs 1H, 7.37–7.05 m (5 H), 4.83 q (1 H), 3.2–0.7 m (16H), 1.51 d (3H).

Example A16

2,6-Diethyl-2,3,6-trimethyl-1-(1-phenyl-ethoxy)-piperidine-4-one oxime-adipic acid ester (Table 1, Comp. 116)

To a stirred suspension of 10.5 g (31.5 mmol) 2,6-diethyl-2,3,6-trimethyl-1-(1-phenyl-ethoxy)-piperidine-4-one oxime in 70 ml toluene are added 4.5 ml (32.5 mmol) of triethylamine and 2.75 g (15 mmol) of adipic acid dichloride. The mixture is stirred for 22 h at room temperature, washed 2× with 50 ml water, dried over MgSO$_4$ and evaporated. The residue is chromatographed on silica gel with hexane-ethyl acetate (5:1) to give 9.35 g (76%) of the title compound as a colorless oil.

$^1$H-NMR (300 MHz, CDCl$_3$): 7.33–7.20 m (10 H), 4.8–4.74 m (2 H), 3.4–0.5 m (58 H)

Example A17

2,6-Diethyl-2,3,6-trimethyl-peridine-4-one oxime-1-oxyl (Table 1, Comp. 117)

In a solution of 4.2 g (20 mmol) 2,6-diethyl-2,3,6-trimethyl-piperidine-4-one oxime (prepared as described by Brunetti, Heimo; Rody, Jean; Sama, Nobuo; Kurumada, Tomoyuki.: Ger. Offen. (1976), DE 2621924) in 20 ml ethylacetate was added dropwise under stirring at room temperature the solution of 7.4 g (30 mmol) of m-chlorperbenzoic acid (70%) in 20 ml of ethyl acetate. The mixture after completed addition is stirred for additional 80 minutes at room temperature, diluted with 100 ml hexane, washed 3× with 1M NaHCO$_3$, dried over MgSO$_4$ and evaporated to give 4.5 g (~100%) of a thick red oil which solidifies upon standing.

Example A18

2,6-Diethyl-2,3,6-trimethyl-piperidine-4-acetoximino-1-oxyl (Table 1, Comp. 118)

a) To a solution of 45.3 g (0.213 mol) of 2,6-diethyl-2,3,6-trimethyl-piperidine-4-one oxime in 40 ml toluene were added 0.2 g 4-dimethylaminopyridin and 20.8 ml acetic anhydride. The mixture was stirred for 75 minutes at 30° C., then diluted with 100 ml toluene, washed with 50 ml 30% NaOH and 50 ml water. The organic layer was dried over MgSO$_4$ and evaporated to give 46.65 g 2,6-diethyl-2,3,6-trimethyl-4-acetoximino-piperidine.

b) To a solution of 25.45 g (0.1 mol) 2,6-Diethyl-2,3,6trimethyl-4-acetoximino-piperidine in 100 ml ethylacetate were under stirring at room temperature added 29.9 ml (0.19 mol) peracetic acid (40% in acetic acid). The mixture for stirred for 22 h at room temperature, diluted with 100 ml hexane, washed with 100 ml water and 100 ml 1 M NaHCO$_3$, dried over MgSO$_4$ and evaporated. The residue was chromatographed on silica gel with hexane-ethylacetate (4:1) to give 12.45 g (46%) of the title compound as a red oil.

For C$_{12}$H$_{13}$N$_2$O$_2$ (227.33) calculated: C, 62.43%; H, 9.35%; N, 10.40%. found 62.46%, H; 9.24%, N; 10.28%.

Example A19

2,6-Diethyl-2,3,6-trimethyl-piperidine-4-one-O-benzyl-oxime-1-oxyl (Table 1, Comp. 119)

A mixture of 25 ml dichloromethane, 26 g of 50% aqueous NaOH, 17.3 ml (0.15 mol) benzyl chloride, 0.66 g (C$_4$H$_9$)$_4$NHSO$_4$ and 22.7 g (0.1 mmol) 2,6-diethyl-2,3,6-trimethyl-piperidine-4-one oxime-1-oxyl is vigorously stirred 12 hours at room temperature. The organic layer is then separated, washed 3× with 20 ml water, dried over MgSO$_4$ and evaporated, at the end at 0.01 mbar/58° C. to give 31.4 g (99%) of the title compound as a red oil.

Example A20

2,6-Diethyl-2,3,6-trimethyl-piperidine-4-one-O-methyl-oxime-1-oxyl (Table 1, Comp. 120)

A mixture of 30 ml dichloromethane, 50 g of 50% aqueous NaOH, 7 ml methyl iodide, 0.35 g (C$_4$H$_9$)$_4$NHSO$_4$ and 1.75 g (7.7 mmol) 2,6-diethyl-2,3,6-trimethyl-piperidine-4-one oxime-1-oxyl is vigorously stirred 5 hours at room temperature. The organic layer is then separated, washed 3× with 20 ml water, dried over MgSO$_4$ and evaporated. The red oily residue is chromatographed on silica gel with hexane-ethylacetate (9:1) to give 1.52 g (82%) of the title compound as a red oil.

The compounds prepared are summarized in table 1.

TABLE 1

| Compound No. | Structure |
|---|---|
| 101 | 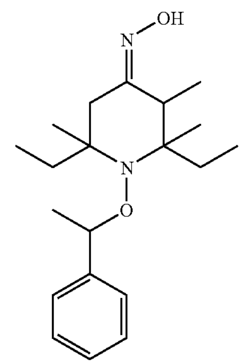 |
| 102 | 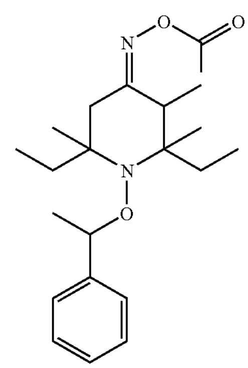 |
| 103 | 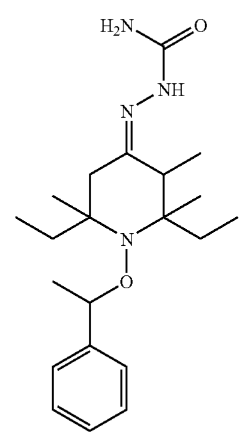 |

TABLE 1-continued
| Compound No. | Structure |
|---|---|
| 104 | 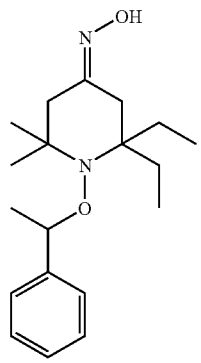 |
| 105 | 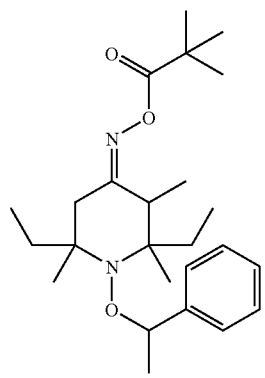 |
| 106 | 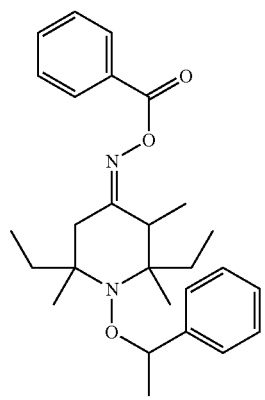 |
| 107 | 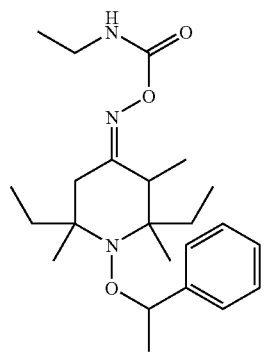 |
| 108 | 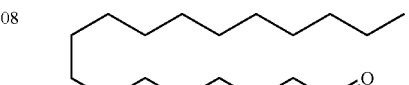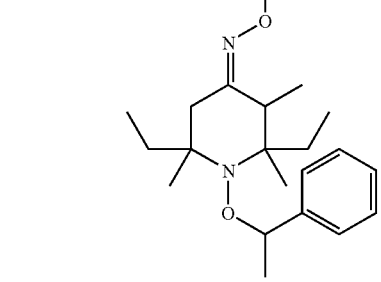 |
| 109 | 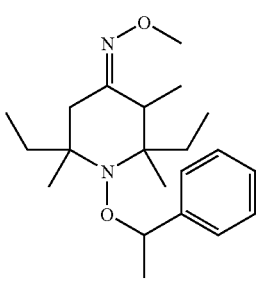 |
| 110 | 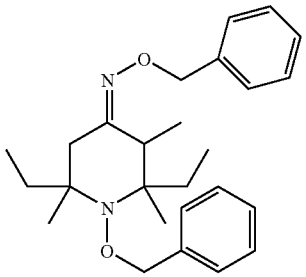 |
| 111 | 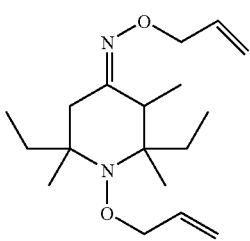 |
| 112 | 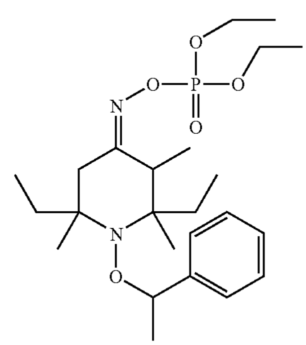 |

TABLE 1-continued

| Compound No. | Structure |
|---|---|
| 113 | (structure) |
| 114 | (structure) |
| 115 | (structure) |
| 116 | (structure) |
| 117 | (structure) |
| 118 | (structure) |
| 119 | (structure) |
| 120 | (structure) |

B) POLYMERIZATION EXAMPLES

General Remarks:

Solvents and monomers are distilled over a Vigreux column under argon atmosphere or under vacuum, shortly before being used.

To remove oxygen all polymerization reaction mixtures are flushed before polymerization with argon and evacuated under vaccum applying a freeze-thaw cycle. The reaction mixtures are then polymerized under argon atmosphere.

At the start of the polymerization reaction, all starting materials are homogeneously dissolved.

Conversion is determined by removing unreacted monomers from the polymer at 80° C. and 0.002 torr for at least 60 minutes, weighing the remaining polymer and subtract the weight of the initiator.

Characterization of the polymers is carried out by MALDI-MS (Matrix Assisted Laser Desorption Ionization Mass Spectrometry) and/or GPC (Gel permeation Chromatography).

MALDI-MS: Measurements are performed on a linear TOF (Time Of Flight) MALDI-MS LDI-1700 Linear Scientific Inc., Reno, USA. The matrix is 2,5-dihydroxybenzoic acid and the laser wavelength is 337 nm.

GPC: Is performed using RHEOS 4000 of FLUX INSTRUMENTS. Tetrahydrofurane (THF) is used as a solvent and is pumped at 1 ml/min. Two chromatography columns are put in series: type plgel 5 µm mixed-C of POLYMER INSTRUMENTS, Shropshire, UK. Measurements are performed at 40° C. The columns are calibrated with low polydispersity polystyrenes having Mn from 200 to 2 000 000 Dalton. Detection is carried out using a RI-Detector ERC-7515A of ERCATECH AG at 30° C.

Example B1

Polymerization of n-butylacrylat with 1.5 mol % of compound 101 (Tabel 1) at 145° C.

In a 50 ml three neck flask, equipped with thermometer, cooler and magnetic stirrer, 1.556 g (4.68 mmol) of compound 101 and 40 g (312 mmol) of n-butylacrylate are mixed and degased. The clear solution obtained is heated under argon to 145° C. and polymerization is carried out during 5 h. The reaction mixture is then cooled to 70° C. The remaining monomer is removed by evaporation under high vacuum. 33.9 g (84.8%) of the initial monomer have reacted. A clear orange viscous fluid is obtained.
$Mn=7600$, $Mw=10260$, $PD=1.35$

Example B2

Polymerization of n-butylacrylat with 1.5 mol % of compound 102 (Tabel 1) at 145° C.

In a 50 ml three neck flask, equipped with thermometer, cooler and magnetic stirrer, 1.753 g (4.68 mmol) of compound 102 and 40 g (312 mmol) of n-butylacrylate are mixed and degased. The clear solution obtained is heated under argon to 145° C. and polymerization is carried out during 5 h. The reaction mixture is then cooled to 70° C. The remaining monomer is removed by evaporation under high vacuum. 31.6 g (79%) of the initial monomer have reacted. A clear orange viscous fluid is obtained.
$Mn=6060$, $Mw=7575$, $PD=1.25$

Example B3

Polymerization of n-butylacrylat with 1.5 mol % of compound 103 (Tabel 1) at 145° C.

In a 50 ml three neck flask, equipped with thermometer, cooler and magnetic stirrer, 438 mg (1.17 mmol) of compound 103 and 10 g (78 mmol) of n-butylacrylate are mixed and degased. The clear solution obtained is heated under argon to 145° C. and polymerization is carried out during 5 h. The reaction mixture is then cooled to 70° C. The remaining monomer is removed by evaporation under high vacuum. 7.7 g (77%) of the initial monomer have reacted. A clear colourless viscous fluid is obtained.
$Mn=9150$, $Mw=12810$, $PD=1.4$

Example B4

Polymerization of n-butylacrylat with 1.5 mol % of compound 104 (Tabel 1) at 145° C.

In a 50 ml three neck flask, equipped with thermometer, cooler and magnetic stirrer, 373 mg (1.17 mmol) of compound 104 and 10 g (78 mmol) of n-butylacrylate are mixed and degased. The clear solution obtained is heated under argon to 145° C. and polymerization is carried out during 5 h. The reaction mixture is then cooled to 70° C. The remaining monomer is removed by evaporation under high vacuum. 6.5 g (65%) of the initial monomer have reacted. A clear colourless viscous fluid is obtained.
$Mn=6380$, $Mw=9890$, $PD=1.55$

Example B5

Polymerization of styrene with 1 mol % of compound 105 (Table 1) at 130° C.

In a 100 ml three neck flask, equipped with thermometer, cooler and magnetic stirrer, 1.816 g (4.36 mmol) of compound 105 and 45.45 g (436 mmol) of styrene are mixed and degased. The clear solution obtained is heated under argon to 130° C. and polymerization is carried out during 6 h. The reaction mixture is then cooled to 80° C. The remaining monomer is removed by evaporation under high vacuum to give 40.45 g (89%) of the polystyrene.
$Mn=7844$, $Mw=9107$, $PD=1.2$

Example B6

Polymerization of styrene with 1 mol % of compound 106 (Table 1) at 130° C.

In a 100 ml three neck flask, equipped with thermometer, cooler and magnetic stirrer, 1.905 g (4.36 mmol) of compound 106 and 45.45 g (436 mmol) of styrene are mixed and degased. The clear solution obtained is heated under argon to 130° C. and polymerization is carried out during 6 h. The reaction mixture is then cooled to 80° C. The remaining monomer is removed by evaporation under high vacuum to give 43.2 g (96%) of the polystyrene.
$Mn=8400$, $Mw=9436$, $PD=1.1$

Example B7

Polymerization of styrene with 1 mol % of compound 107 (Table 1) at 130° C.

In a 100 ml three neck flask, equipped with thermometer, cooler and magnetic stirrer, 1.759 g (4.36 mmol) of compound 107 and 45.45 g (436 mmol) of styrene are mixed and degased. The clear solution obtained is heated under argon to 130° C. and polymerization is carried out during 6 h. The reaction mixture is then cooled to 80° C. The remaining monomer is removed by evaporation under high vacuum to give 39 g (86%) of the polystyrene.
$Mn=7907$, $Mw=9162$, $PD=1.2$

Example B8

Polymerization of styrene with 1 mol % of compound 108 (Table 1) at 130° C.

In a 100 ml three neck flask, equipped with thermometer, cooler and magnetic stirrer, 2.611 g (4.36 mmol) of compound 108 and 45.45 g (436 mmol) of styrene are mixed and degased. The clear solution obtained is heated under argon to 130° C. and polymerization is carried out during 6 h. The reaction mixture is then cooled to 80° C. The remaining monomer is removed by evaporation under high vacuum to give 39 g (86%) of the polystyrene.
$Mn=8616$, $Mw=9952$, $PD=1.2$

Example B9

Polymerization of styrene with 1 mol % of compound 109 (Table 1) at 130° C.

In a 100 ml three neck flask, equipped with thermometer, cooler and magnetic stirrer, 1.511 g (4.36 mmol) of compound 109 and 45.45 g (436 mmol) of styrene are mixed and degased. The clear solution obtained is heated under argon to 130° C. and polymerization is carried out during 6 h. The reaction mixture is then cooled to 80° C. The remaining monomer is removed by evaporation under high vacuum to give 37.3 g (82%) of the polystyrene.
Mn=7882, Mw=8820, PD=1.1

Example B10

Reinitiation of poly-styrene terminated with Compound 101 with n-butylacrylate

In a dry, argon-purged Schlenk tube 2.5 g of polystyrene terminated with Compound 101 are dissolved in 15 g n-butylacrylate. The mixture is degassed in three consecutive freeze-thaw-cycles and purged with argon. The stirred solution is then immersed in an oil bath and heated to 145° C. for 6 h. The residual monomer is then removed under vacuum at 40° C. and the blockcopolymer is dried at 40° C. in vacuum until constant weight is achieved. Conversion referred to the monomer (n-butylacrylate) is 36.2%. The molecular weight ($M_p$) increased from 9300 g/mol (Cmpd 101-term-PS) to 47300 g/mol (PS-b-PBuA) and the polydispersity from 1.2 to 1.8.

Example B11

Reinitiation of a poly-n-butylacrylate terminated with Compound 101 with styrene In a dry, argon-purged Schlenk tube 2.5 g of poly-n-butylacrylate terminated with Compound 101 are dissolved in 15 g styrene. The mixture is degassed in three consecutive freeze-thaw-cycles and purged with argon. The stirred solution is then immersed in an oil bath and heated to 130° C. for 6 h. The residual monomer is then removed under vacuum at 40° C. and the blockcopolymer is dried at 40° C. in vacuum until constant weight is achieved. Conversion referred to the monomer (styrene) is 66.0%. The molecular weight ($M_p$) increased from 8600 g/mol (CG 41-0330-term-PBuA) to 47500 g/mol (PBuA-b-PS) and the polydispersity from 1.3 to 1.5.

The invention claimed is:
1. A compound of formula (I)

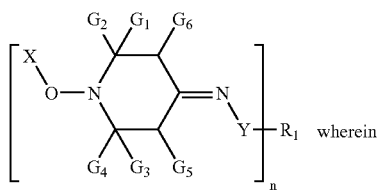

wherein $G_1$, $G_2$, $G_3$ and $G_4$ are independently $C_1$–$C_4$alkyl or $G_1$ and $G_2$ together and $G_3$ and $G_4$ together, or $G_1$ and $G_2$ together or $G_3$ and $G_4$ together are pentamethylene; wherein, when $G_1$, $G_2$, $G_3$ and $G_4$ are $C_1$–$C_4$alkyl, at least one is higher alkyl than methyl;

$G_5$ and $G_6$ are each independently of the other hydrogen or $C_1$–$C_4$alkyl;

n is 1, 2, 3, or 4;

Y is O or $NR_2$ or when n is 1 and $R_1$ represents alkyl or aryl, Y is additionally a direct bond;

$R_2$ is H, $C_1$–$C_{18}$alkyl or phenyl;

if n is 1, $R_1$ is H, straight or branched $C_1$–$C_{18}$alkyl, $C_3$–$C_{18}$alkenyl or $C_3$–$C_{18}$alkinyl, which may be unsubstituted or substitued by one or more OH, $C_1$–$C_8$alkoxy, carboxy or $C_1$–$C_8$alkoxycarbonyl;

$C_5$–$C_{12}$cycloalkyl or $C_5$–$C_{12}$cycloalkenyl;

phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy or $C_1$–$C_8$alkoxycarbonyl;

—C(O)—$C_1$–$C_{36}$alkyl, or an acyl moiety of a α,β-unsaturated carboxylic acid having 3 to 5 carbon atoms or of an aromatic carboxylic acid having 7 to 15 carbon atoms;

—$SO_3^-Q^+$, —$PO(O^-Q^+)_2$, —$P(O)(OR_2)_2$, —$SO_2$—$R_2$, —CO—NH—$R_2$, —$CONH_2$, $COOR_2$ or $Si(Me)_3$, wherein $Q^+$ is $H^+$, ammnonium or an alkali metal cation;

if n is 2, $R_1$ is $C_1$–$C_{18}$alkylene, $C_3$–$C_{18}$alkenylene or $C_3$–$C_{18}$alkinylene, which may be unsubstituted or substitued by one or more OH, $C_1$–$C_8$alkoxy, carboxy or $C_1$–$C_8$alkoxycarbonyl;

or xylylene; or $R_1$ is a bisacyl radical of an aliphatic dicarboxylic acid having 2 to 36 carbon atoms, or a cycloaliphatic or aromatic dicarboxylic acid having 8–14 carbon atoms;

if n is 3, $R_1$ is a trivalent radical of an aliphatic, cycloaliphatic or aromatic tricarboxylic acid;

if n is 4, $R_1$ is a tetravalent radical of an aliphatic, cycloaliphatic or aromatic tetracarboxylic acid;

and

X is selected from the group consisting of

—$CH_2$-aryl,

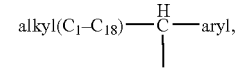

—$CH_2$—$CH_2$-aryl,

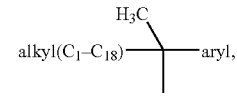

$(C_5$–$C_6$cycloalkyl$)_2$CCN, $(C_1$–$C_{12}$alkyl$)_2$CCN,
—$CH_2CH$=$CH_2$, $(C_1$–$C_{12})$alkyl-$CR_{20}$—C(O)—$(C_1$–$C_{12})$alkyl, $(C_1-C_{12})$alkyl-$CR_{20}$—C(O)—$(C_6-C_{10})$aryl, $(C_1-C_{12})$alkyl-$CR_{20}$—C(O)—$(C_1-C_{12})$alkoxy, $(C_1-C_{12})$alkyl-$CR_{20}$—C(O)-phenoxy, $(C_1-C_{12})$alkyl-$CR_{20}$—C(O)—N-di$(C_1-C_{12})$alkyl, $(C_1-C_{12})$alkyl-$CR_{20}$—CO—NH$(C_1-C_{12})$alkyl, $(C_1-C_{12})$alkyl-$CR_{20}$—CO—NH$_2$, —$CH_2CH$=CH—$CH_3$, —$CH_2$—C($CH_3$)=$CH_2$, —$CH_2$—CH=CH-phenyl,

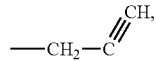

3-cyclohexenyl, 3-cyclopentenyl,

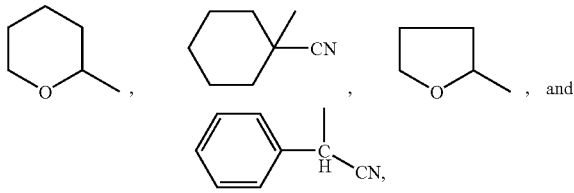

wherein $R_{20}$ is hydrogen or $C_1-C_{12}$alkyl;

the alkyl groups are unsubstituted or substituted with one or more —OH, —COOH or —C(O)$R_{20}$ groups; and the aryl groups are phenyl or naphthyl which are unsubstituted or substituted with $C_1-C_{12}$alkyl, halogen, $C_1-C_{12}$alkoxy, $C_1-C_{12}$alkylcarbonyl, glycidyloxy, OH, —COOH or —COO$(C_1-C_{12})$alkyl.

2. A compound according to claim 1 wherein X is selected from the group consisting of —$CH_2$-phenyl, $CH_3CH$-phenyl, $(CH_3)_2C$-phenyl, $(C_5-C_6$cycloalkyl$)_2$CCN, $(CH_3)_2$CCN,

—$CH_2CH$=$CH_2$, $CH_3CH$—CH=$CH_2$, $(C_1-C_8$alkyl$)CR_{20}$—C(O)-phenyl, $(C_1-C_8)$alkyl-$CR_{20}$—C(O)—$(C_1-C_8)$alkyl-$CR_{20}$—C(O)—$(C_1-C_8)$alkyl, $(C_1-C_8)$alkyl-$CR_{20}$—C(O)—N-di$(C_1-C_8)$alkyl, $(C_1-C_8)$alkyl-$CR_{20}$—C(O)—NH$(C_1-C_8)$alkyl and $(C_1-C_8)$alkyl-$CR_{20}$—C(O)—NH$_2$, wherein $R_{20}$ is hydrogen or $(C_1-C_8)$alkyl.

3. A compound according to claim 2 wherein X is selected from the group consisting of —$CH_2$-phenyl, $CH_3CH$-phenyl, $(CH_3)_2C$-phenyl, $(C_5-C_8$cycloalkyl$)_2$CCN, $(CH_3)_2$CCN, or

—$CH_2CH$=$CH_2$, $CH_3CH$—CH=$CH_2$ $(C_1-C_4$alkyl$)$$CR_{20}$—C(O)-phenyl, $(C_1-C_4)$alkyl-$CR_{20}$—C(O)—$(C_1-C_4)$alkyl-$CR_{20}$—C(O)—$(C_1-C_4)$alkyl, $(C_1-C_4)$alkyl-$CR_{20}$—C(O)—N-di$(C_1-C_4)$alkyl, $(C_1-C_4)$alkyl-$CR_{20}$—C(O)—NH$(C_1-C_4)$alkyl and $(C_1-C_4)$alkyl-$CR_{20}$—C(O)—NH$_2$, wherein $R_{20}$ is hydrogen or $(C_1-C_4)$alkyl.

4. A compound according to claim 1 wherein at least one of $G_1$, $G_2$, $G_3$ and $G_4$ is ethyl and the others are methyl and $G_5$ and $G_6$ are each independently of the other hydrogen or methyl.

5. A compound according to claim 1 wherein Y is O.

6. A compound according to claim 1 wherein $G_1$ and $G_3$ are methyl and $G_2$ and $G_4$ are ethyl, or $G_1$ and $G_2$ are methyl and $G_3$ and $G_4$ are ethyl;

$G_5$ and $G_6$ are each independently of the other hydrogen or methyl; and

Y is O;

n is 1, $R_1$ is H, straight or branched $C_1-C_{18}$alkyl or $C_3-C_{18}$alkenyl;

$C_5-C_{12}$cycloalkyl or $C_5-C_{12}$cycloalkenyl;

phenyl, $C_7-C_9$phenylalkyl or naphthyl which may be unsubstituted or substituted by one or more $C_1-C_8$alkyl, halogen, OH or $C_1-C_8$alkoxy; or —C(O)—$C_1-C_{36}$alkyl, or an acyl moiety of a α,β-unsaturated carboxylic acid having 3 to 5 carbon atoms or of an aromatic carboxylic acid having 7 to 15 carbon atoms; and X is selected from the group consisting of
—$CH_2$-phenyl, $CH_3CH$-phenyl, $(CH_3)_2C$-phenyl, $(C_5-C_6$cycloalkyl$)_2$CCN, $(CH_3)_2$CCN,

—$CH_2CH$=$CH_2$, $CH_3CH$—CH=$CH_2$ $(C_1-C_4$alkyl$)$$CR_{20}$—C(O)-phenyl, $(C_1-C_4)$alkyl-$CR_{20}$—C(O)—$(C_1-C_4)$alkoxy, $(C_1C_4)$alkyl-$CR_{20}$—C(O)—$(C_1-C_4)$alkyl, $(C_1-C_4)$alkyl-$CR_{20}$—C(O)—N-di$(C_1-C_4)$alkyl, $(C_1-C_4)$alkyl-$CR_{20}$—C(O)—NH$(C_1-C_4)$alkyl and $(C_1-C_4)$alkyl-$CR_{20}$—C(O)—NH$_2$, wherein $R_{20}$ is hydrogen or $(C_1-C_4)$alkyl.

7. A compound according to claim 1 which is
a) 2,6-Diethyl-2,3,6-trimethyl-1-(1-phenyl-ethoxy)-piperidine-4-one oxime,
b) 2,6-Diethyl-2,3,6-trimethyl-1-(1-phenyl-ethoxy)-4-acetoximino-piperidine,
c) 2,2-Diethyl-6,6-dimethyl-1-(1-phenyl-ethoxy)-piperidine-4-one oxime,
d) 2,6-Diethyl-2,3,6-trimethyl-1-(1-phenyl-ethoxy)-4-pivaloyloximino-piperidine or
e) 2,6-Diethyl-2,3,6-trimethyl-1-(1-phenyl-ethoxy)-4-benzoyloximino-piperidine.

8. A polymerizable composition, comprising
a) at least one ethylenically unsaturated monomer or oligomer, and
b) a compound according to formula (I)

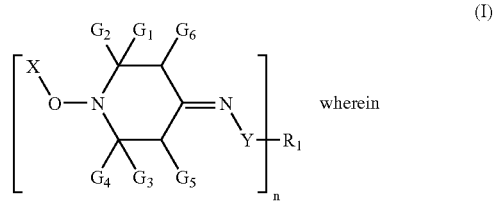

wherein $G_1$, $G_2$, $G_3$ and $G_4$ are independently $C_1$–$C_4$alkyl or $G_1$ and $G_2$ together and $G_3$ and $G_4$ together, or $G_1$ and $G_2$ together or $G_3$ and $G_4$ together are pentamethylene;

$G_5$ and $G_6$ are each independently of the other hydrogen or $C_1$–$C_4$alkyl; and X represents a group such that the free radical X. derived from X is capable of initiating polymerization of ethylenically unsaturated monomers;

n is 1, 2, 3, or 4;

Y is O or $NR_2$ or when n is 1 and $R_1$ represents alkyl, or aryl Y is additionally a direct bond;

$R_2$ is H, $C_1$–$C_{18}$alkyl or phenyl;

if n is 1, $R_1$ is H, straight or branched $C_1$–$C_{18}$alkyl, $C_3$–$C_{18}$alkenyl or $C_3$–$C_{18}$alkinyl, which may be unsubstituted or substituted by one or more OH, $C_1$–$C_8$alkoxy, carboxy or $C_1$–$C_8$alkoxycarbonyl;

$C_5$–$C_{12}$cycloalkyl or $C_5$–$C_{12}$cycloalkenyl;

phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy or $C_1$–$C_8$alkoxycarbonyl;

—C(O)—$C_1$–$C_{36}$alkyl, or an acyl moiety of a α,β-unsaturated carboxylic acid having 3 to 5 carbon atoms or of an aromatic carboxylic acid having 7 to 15 carbon atoms;

—$SO_3^-Q^+$, —$PO(O^-Q^+)_2$, —$P(O)(OR_2)_2$, —$SO_2$—$R_2$, —CO—NH—$R_2$, —$CONH_2$, $COOR_2$ or $Si(Me)_3$, wherein $Q^+$ is $H^+$, ammnonium or an alkali metal cation;

if n is 2, $R_1$ is $C_1$–$C_{18}$alkylene, $C_3$–$C_{18}$alkenylene or $C_3$–$C_8$alkinylene, which may be unsubstituted or substituted by one or more OH, $C_1$–$C_8$alkoxy, carboxy or $C_1$–$C_8$alkoxycarbonyl;

or xylylene; or $R_1$ is a bisacyl radical of an aliphatic dicarboxylic acid having 2 to 36 carbon atoms, or a cycloaliphatic or aromatic dicarboxylic acid having 8–14 carbon atoms;

if n is 3, $R_1$ is a trivalent radical of an aliphatic, cycloaliphatic or aromatic tricarboxylic acid; and if n is 4, $R_1$ is a tetravalent radical of an aliphatic, cycloaliphatic or aromatic tetracarboxylic acid.

9. A composition according to claim 8, wherein the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl)acrylic acid salts, (alkyl)acrylic esters, (meth)acrylonitriles, (alkyl)acrylamides, vinyl halides and vinylidene halides.

10. A composition according to claim 8, wherein the initiator compound is present in an amount of from 0.01 mol-% to 20 mol-%, based on the monomer or monomer mixture.

11. A process for preparing an oligomer, a cooligomer, a polymer or a copolymer (block or random) by free radical polymerization of at least one ethylenically unsaturated monomer or oligomer, which comprises (co)polymerizing the monomer or monomers/oligomers in the presence of an initiator compound of formula (I)

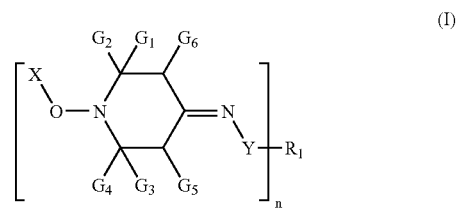

under reaction conditions capable of effecting scission of the O—C bond to form two free radicals, the radical .X being capable of initiating polymerization;

where $G_1$, $G_2$, $G_3$ and $G_4$ are independently $C_1$–$C_4$alkyl or $G_1$ and $G_2$ together and $G_3$ and $G_4$ together, or $G_1$ and $G_2$ together or $G_3$ and $G_4$ together are pentamethylene;

$G_5$ and $G_6$ are each independently of the other hydrogen or $C_1$–$C_4$alkyl; and X represents a group such that the free radical X. derived from X is capable of initiating polymerization of ethylenically unsaturated monomers;

n is 1, 2, 3, or 4;

Y is O or $NR_2$ or when n is 1 and $R_1$ represents alkyl or aryl, Y is additionally a direct bond;

$R_2$ is H, $C_1$–$C_{18}$alkyl or phenyl;

if n is 1, $R_1$ is H, straight or branched $C_1$–$C_{18}$alkyl, $C_3$–$C_{18}$alkenyl or $C_3$–$C_{18}$alkinyl, which may be unsubstituted or substituted by one or more OH, $C_1$–$C_8$alkoxy, carboxy or $C_1$–$C_8$alkoxycarbonyl;

$C_5$–$C_{12}$cycloalkyl or $C_5$–$C_{12}$cycloalkenyl;

phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy or $C_1$–$C_8$alkoxycarbonyl;

—C(O)—$C_1$–$C_{36}$alkyl, or an acyl moiety of a α,β-unsaturated carboxylic acid having 3 to 5 carbon atoms or of an aromatic carboxylic acid having 7 to 15 carbon atoms;

—$SO_3^-Q^+$, —$PO(O^-Q^+)_2$, —$P(O)(OR_2)_2$, —$SO_2$—$R_2$, —CO—NH—$R_2$, —$CONH_2$, $COOR_2$ or $Si(Me)_3$, wherein $Q^+$ is $H^+$, ammonium or an alkali metal cation;

if n is 2, $R_1$ is $C_1$–$C_{18}$alkylene, $C_3$–$C_{18}$alkenylene or $C_3$–$C_{18}$alkinylene, which may be unsubstituted or substituted by one or more OH, $C_1$–$C_8$alkoxy, carboxy or $C_1$–$C_8$alkoxycarbonyl;

or xylylene; or $R_1$ is a bisacyl radical of an aliphatic dicarboxylic acid having 2 to 36 carbon atoms, or a cycloaliphatic or aromatic dicarboxylic acid having 8–14 carbon atoms;

if n is 3, $R_1$ is a trivalent radical of an aliphatic, cycloaliphatic or aromatic tricarboxylic acid; and if n is 4, $R_1$ is a tetravalent radical of an aliphatic, cycloaliphatic or aromatic tetracarboxylic acid.

12. A process according to claim 11, wherein the scission of the O—C bond is effected by ultrasonic treatment, heating or exposure to electromagnetic radiation, ranging from γ to microwaves.

13. A process according to claim 11, wherein the scission of the O—C bond is effected by heating and takes place at a temperature of between 50° C. and 160° C.

14. A compound according to formula (II)

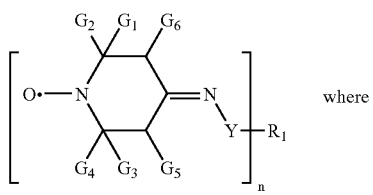
(II)

where $G_1$ and $G_3$ are independently $C_1$–$C_4$alkyl;
$G_2$ and $G_4$ are independently $C_2$–$C_4$alkyl;
$G_5$ and $G_6$ are each independently of the other hydrogen or $C_1$–$C_4$alkyl;
n is 1, 2, 3, or 4,
Y is O or $NR_2$;
$R_2$ is H, $C_1$–$C_{18}$alkyl or phenyl;
if n is 1,
$R_1$ is H, straight or branched $C_1$–$C_{18}$alkyl, $C_3$–$C_{18}$alkenyl or $C_3$–$C_{18}$alkinyl, which may be unsubstituted or substituted by one or more OH, $C_1$–$C_8$alkoxy, carboxy or $C_1$–$C_8$alkoxycarbonyl;
$C_5$–$C_{12}$cycloalkyl or $C_5$–$C_{12}$cycloalkenyl;
phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy or $C_1$–$C_8$alkoxycarbonyl;
—C(O)—$C_1$–$C_{36}$alkyl, or an acyl moiety of a α,β-unsaturated carboxylic acid having 3 to 5 carbon atoms or of an aromatic carboxylic acid having 7 to 15 carbon atoms;
—$SO_3^-Q^+$, —$PO(O^-Q^+)_2$, —$P(O)(OR_2)_2$, —$SO_2$—$R_2$, —CO—NH—$R_2$, —$CONH_2$, $COOR_2$ or $Si(Me)_3$, wherein $Q^+$ is $H^+$, ammnonium or an alkali metal cation;
if n is 2,
$R_1$ is $C_1$–$C_{18}$alkylene, $C_3$–$C_{18}$alkenylene or $C_3$–$C_{18}$alkinylene, which may be unsubstituted or substituted by one or more OH, $C_1$–$C_8$alkoxy, carboxy or $C_1$–$C_8$alkoxycarbonyl;
or xylylene; or
$R_1$ is a bisacyl radical of an aliphatic dicarboxylic acid having 2 to 36 carbon atoms, or a cycloaliphatic or aromatic dicarboxylic acid having 8–14 carbon atoms;
if n is 3,
$R_1$ is a trivalent radical of an aliphatic, cycloaliphatic or aromatic tricarboxylic acid; and
if n is 4,
$R_1$ is a tetravalent radical of an aliphatic, cycloaliphatic or aromatic tetracarboxylic acid.

15. A polymerizable composition, comprising
a) at least one ethylenically unsaturated monomer or oligomer, and
b) a compound according to formula (II)

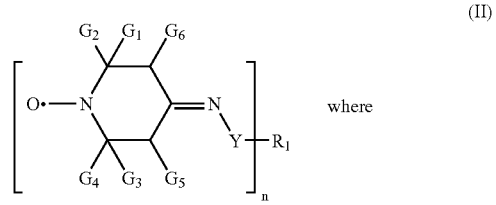
(II)

where $G_1$, $G_2$, $G_3$ and $G_4$ are independently $C_1$–$C_4$alkyl or $G_1$ and $G_2$ together and $G_3$ and $G_4$ together, or $G_1$ and $G_2$ together or $G_3$ and $G_4$ together are pentamethylene;
$G_5$ and $G_6$ are each independently of the other hydrogen or $C_1$–$C_4$alkyl;
n is 1, 2, 3, or 4;
Y is O or $NR_2$ or when n is 1 and $R_1$ represents alkyl or aryl, Y is additionally a direct bond;
$R_2$ is H, $C_1$–$C_{18}$alkyl or phenyl;
if n is 1,
$R_1$ is H, straight or branched $C_1$–$C_{18}$alkyl, $C_3$–$C_{18}$alkenyl or $C_3$–$C_{18}$alkinyl, which may be unsubstituted or substituted by one or more OH, $C_1$–$C_8$alkoxy, carboxy or $C_1$–$C_8$alkoxycarbonyl;
$C_5$–$C_{12}$cycloalkyl or $C_5$–$C_{12}$cycloalkenyl;
phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy or $C_1$–$C_8$alkoxycarbonyl;
—C(O)—$C_1$–$C_{36}$alkyl, or an acyl moiety of a α,β-unsaturated carboxylic acid having 3 to 5 carbon atoms or of an aromatic carboxylic acid having 7 to 15 carbon atoms;
—$SO_3^-Q^+$, —$PO(O^-Q^+)_2$, —$P(O)(OR_2)_2$, —$SO_2$—$R_2$, —CO—NH—$R_2$, —$CONH_2$, $COOR_2$ or $Si(Me)_3$, wherein $Q^+$ is $H^+$, ammnonium or an alkali metal cation;
if n is 2,
$R_1$ is $C_1$–$C_{18}$alkylene, $C_3$–$C_{18}$alkenylene or $C_3$–$C_{18}$alkinylene, which may be unsubstituted or substituted by one or more OH, $C_1$–$C_8$alkoxy, carboxy or $C_1$–$C_8$alkoxycarbonyl;
or xylylene; or
$R_1$ is a bisacyl radical of an aliphatic dicarboxylic acid having 2 to 36 carbon atoms, or a cycloaliphatic or aromatic dicarboxylic acid having 8–14 carbon atoms;
if n is 3,
$R_1$ is a trivalent radical of an aliphatic, cycloaliphatic or aromatic tricarboxylic acid; and
if n is 4,
$R_1$ is a tetravalent radical of an aliphatic, cycloaliphatic or aromatic tetracarboxylic acid; and
c) source of free radicals.

16. A composition according to claim 15, wherein the compound of formula (II) is present in an amount of from 0.01 mol-% to 20 mol-%, based on the monomer or monomer mixture.

17. A composition according to claim 15, wherein the free radical source is present in an amount of from 0.01 mol-% to 20 mol-%, based on the monomer or monomer mixture.

18. A composition according to claim 15 wherein the molar ratio of the radical source to the compound of formula II may be from 1:10 to 10:1.

19. A process for preparing an oligomer, a cooligomer, a polymer or a copolymer (block or random) by free radical polymerization of at least one ethylenically unsaturated monomer or oligomer, which comprises (co)polymerizing the monomer or monomers/oligomers in the presence of a compound of formula (II)

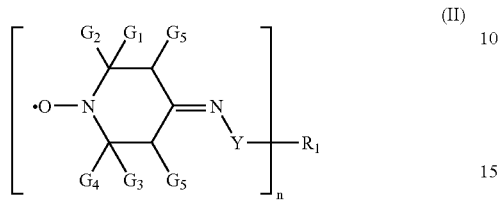

and a source of free radicals, the radials being capable of initiating polymerization;
where
$G_1$, $G_2$, $G_3$ and $G_4$ are independently $C_1$–$C_4$alkyl or $G_1$ and $G_2$ together and $G_3$ and $G_4$ together, or $G_1$ and $G_2$ together or $G_3$ and $G_4$ together are pentamethylene;
$G_5$ and $G_6$ are each independently of the other hydrogen or $C_1$–$C_4$alkyl;
n is 1, 2, 3, or 4;
Y is O or $NR_2$ or when n is 1 and $R_1$ represents alkyl or aryl, Y is additionally a direct bond;
$R_2$ is H, $C_1$–$C_{18}$alkyl or phenyl;
if n is 1,
$R_1$ is H, straight or branched $C_1$–$C_{18}$alkyl, $C_3$–$C_{18}$alkenyl or $C_3$–$C_{18}$alkinyl, which may be unsubstituted or substituted by one or more OH, $C_1$–$C_8$alkoxy, carboxy or $C_1$–$C_8$alkoxycarbonyl;
$C_5$–$C_{12}$cycloalkyl or $C_5$–$C_{12}$cycloalkenyl;
phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy or $C_1$–$C_8$alkoxycarbonyl;
—C(O)—$C_1$–$C_{36}$alkyl, or an acyl moiety of a α,β-unsaturated carboxylic acid having 3 to 5 carbon atoms or of an aromatic carboxylic acid having 7 to 15 carbon atoms;
—$SO_3^-Q^+$, —$PO(O^-Q^+)_2$, —$P(O)(OR_2)_2$, —$SO_2$—$R_2$, —CO—NH—$R_2$, —$CONH_2$, $COOR_2$ or $Si(Me)_3$, wherein $Q^+$ is $H^+$, ammnonium or an alkali metal cation;
if n is 2,
$R_1$ is $C_1$–$C_{18}$alkylene, $C_3$–$C_{18}$alkenylene or $C_3$–$C_{18}$alkinylene, which may be unsubstituted or substituted by one or more OH, $C_1$–$C_8$alkoxy, carboxy or $C_1$–$C_8$alkoxycarbonyl;
or xylylene; or
$R_1$ is a bisacyl radical of an aliphatic dicarboxylic acid having 2 to 36 carbon atoms, or a cycloaliphatic or aromatic dicarboxylic acid having 8–14 carbon atoms;
if n is 3,
$R_1$ is a trivalent radical of an aliphatic, cycloaliphatic or aromatic tricarboxylic acid; and
if n is 4,
$R_1$ is a tetravalent radical of an aliphatic, cycloaliphatic or aromatic tetracarboxylic acid.

20. A polymer prepared by radical polymerization according to claim 11 having attached a group

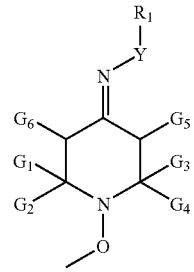

where
$G_1$, $G_2$, $G_3$ and $G_4$ are independently $C_1$–$C_4$alkyl or $G_1$ and $G_2$ together and $G_3$ and $G_4$ together, or $G_1$ and $G_2$ together or $G_3$ and $G_4$ together are pentamethylene;
$G_5$ and $G_6$ are each independently of the other hydrogen or $C_1$–$C_4$alkyl; and
X represents a group such that the free radical X. derived from X is capable of initiating polymerization of ethylenically unsaturated monomers;
n is 1, 2, 3, or 4;
Y is O or $NR_2$ or when n is 1 and $R_1$ represents alkyl or aryl, Y is additionally a direct bond;
$R_2$ is H, $C_1$–$C_{18}$alkyl or phenyl;
if n is 1,
$R_1$ is H, straight or branched $C_1$–$C_{18}$alkyl, $C_3$–$C_{18}$alkenyl or $C_3$–$C_{18}$alkinyl, which may be unsubstituted or substituted by one or more OH, $C_1$–$C_8$alkoxy, carboxy or $C_1$–$C_8$alkoxycarbonyl;
$C_5$–$C_{12}$cycloalkyl or $C_5$–$C_{12}$cycloalkenyl;
phenyl, $C_7$–$C_9$phenylalkyl or naphthyl which may be unsubstituted or substituted by one or more $C_1$–$C_8$alkyl, halogen, OH, $C_1$–$C_8$alkoxy, carboxy or $C_1$–$C_8$alkoxycarbonyl;
—C(O)—$C_1$–$C_{36}$alkyl, or an acyl moiety of a α,β-unsaturated carboxylic acid having 3 to 5 carbon atoms or of an aromatic carboxylic acid having 7 to 15 carbon atoms;
—$SO_3^-Q^+$, —$PO(O^-Q^+)_2$, —$P(O)(OR_2)_2$, —$SO_2$—$R_2$, —CO—NH—$R_2$, —$CONH_2$, $COOR_2$ or $Si(Me)_3$, wherein $Q^+$ is $H^+$, ammnonium or an alkali metal cation;
if n is 2,
$R_1$ is $C_1$–$C_{18}$alkylene, $C_3$–$C_{18}$alkenylene or $C_3$–$C_{18}$alkinylene, which may be unsubstituted or substituted by one or more OH, $C_1$–$C_8$alkoxy, carboxy or $C_1$–$C_8$alkoxycarbonyl;
or xylylene; or
$R_1$ is a bisacyl radical of an aliphatic dicarboxylic acid having 2 to 36 carbon atoms, or a cycloaliphatic or aromatic dicarboxylic acid having 8–14 carbon atoms;
if n is 3,
$R_1$ is a trivalent radical of an aliphatic, cycloaliphatic or aromatic tricarboxylic acid; and
if n is 4,
$R_1$ is a tetravalent radical of an aliphatic, cycloaliphatic or aromatic tetracarboxylic acid.

21. An improved process for the preparation of a compound of formula (I)

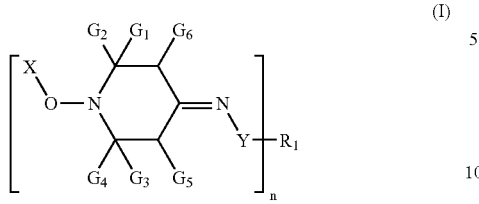

comprising reacting a compound of formula (X)

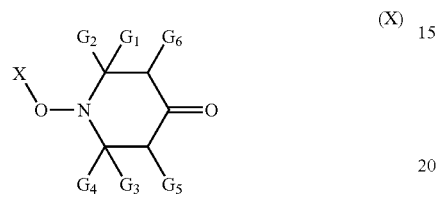

with a compound of formula (XI), $$R_1\text{—}Y\text{—}NH_2 \quad (XI)$$

characterized in that the compound of formula X is firstly treated with an acid or base catalyst or the acid or base catalyst is added during the imine forming reaction;
where
- $G_1$, $G_2$, $G_3$ and $G_4$ are independently $C_1\text{–}C_4$alkyl or $G_1$ and $G_2$ together and $G_3$ and $G_4$ together, or $G_1$ and $G_2$ together or $G_3$ and $G_4$ together are pentamethylene;
- $G_5$ and $G_6$ are each independently of the other hydrogen or $C_1\text{–}C_4$alkyl; and
- X represents a group such that the free radical X. derived from X is capable of initiating polymerization of ethylenically unsaturated monomers;
- n is 1, 2, 3, or 4;
- Y is O or $NR_2$ or when n is 1 and $R_1$ represents alkyl or aryl, Y is additionally a direct bond;
- $R_2$ is H, $C_1\text{–}C_{18}$alkyl or phenyl;
- if n is 1,
- $R_1$ is H, straight or branched $C_1\text{–}C_{18}$alkyl, $C_3\text{–}C_{18}$alkenyl or $C_3\text{–}C_{18}$alkinyl, which may be unsubstituted or substituted by one or more OH, $C_1\text{–}C_8$alkoxy, carboxy or $C_1\text{–}C_8$alkoxycarbonyl;
- $C_5\text{–}C_{12}$cycloalkyl or $C_5\text{–}C_{12}$cycloalkenyl;
- phenyl, $C_7\text{–}C_9$phenylalkyl or naphthyl which may be unsubstituted or substituted by one or more $C_1\text{–}C_8$alkyl, halogen, OH, $C_1\text{–}C_8$alkoxy, carboxy or $C_1\text{–}C_8$alkoxycarbonyl;
- —C(O)—$C_1\text{–}C_{36}$alkyl, or an acyl moiety of a α,β-unsaturated carboxylic acid having 3 to 5 carbon atoms or of an aromatic carboxylic acid having 7 to 15 carbon atoms;
- —$SO_3^-Q^+$, —$PO(O^-Q^+)_2$, —$P(O)(OR_2)_2$, —$SO_2$—$R_2$, —CO—NH—$R_2$, —$CONH_2$, $COOR_2$ or $Si(Me)_3$, wherein $Q^+$ is $H^+$, ammnonium or an alkali metal cation;
- if n is 2,
- $R_1$ is $C_1\text{–}C_{18}$alkylene, $C_3\text{–}C_{18}$alkenylene or $C_3\text{–}C_{18}$alkinylene, which may be unsubstituted or substituted by one or more OH, $C_1\text{–}C_8$alkoxy, carboxy or $C_1\text{–}C_8$alkoxycarbonyl;
- or xylylene; or
- $R_1$ is a bisacyl radical of an aliphatic dicarboxylic acid having 2 to 36 carbon atoms, or a cycloaliphatic or aromatic dicarboxylic acid having 8–14 carbon atoms;
- if n is 3,
- $R_1$ is a trivalent radical of an aliphatic, cycloaliphatic or aromatic tricarboxylic acid; and
- if n is 4,
- $R_1$ is a tetravalent radical of an aliphatic, cycloaliphatic or aromatic tetracarboxylic acid.

22. A polymer prepared by radical polymerization according to claim 19 having attached a group

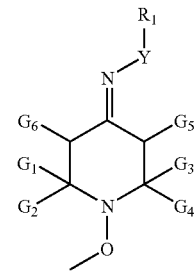

where
- $G_1$, $G_2$, $G_3$ and $G_4$ are independently $C_1\text{–}C_4$alkyl or $G_1$ and $G_2$ together and $G_3$ and $G_4$ together, or $G_1$ and $G_2$ together or $G_3$ and $G_4$ together are pentamethylene;
- $G_5$ and $G_6$ are each independently of the other hydrogen or $C_1\text{–}C_4$alkyl; and
- X represents a group such that the free radical X. derived from X is capable of initiating polymerization of ethylenically unsaturated monomers;
- n is 1, 2, 3, or 4;
- Y is O or $NR_2$ or when n is 1 and $R_1$ represents alkyl or aryl, Y is additionally a direct bond;
- $R_2$ is H, $C_1\text{–}C_{18}$alkyl or phenyl;
- if n is 1,
- $R_1$ is H, straight or branched $C_1\text{–}C_{18}$alkyl, $C_3\text{–}C_{18}$alkenyl or $C_3\text{–}C_{18}$alkinyl, which may be unsubstituted or substituted by one or more OH, $C_1\text{–}C_8$alkoxy, carboxy or $C_1\text{–}C_8$alkoxycarbonyl;
- $C_5\text{–}C_{12}$cycloalkyl or $C_5\text{–}C_{12}$cycloalkenyl;
- phenyl, $C_7\text{–}C_9$phenylalkyl or naphthyl which may be unsubstituted or substituted by one or more $C_1\text{–}C_8$alkyl, halogen, OH, $C_1\text{–}C_8$alkoxy, carboxy or $C_1\text{–}C_8$alkoxycarbonyl;
- —C(O)—$C_1\text{–}C_{36}$alkyl, or an acyl moiety of a α,β-unsaturated carboxylic acid having 3 to 5 carbon atoms or of an aromatic carboxylic acid having 7 to 15 carbon atoms;
- —$SO_3^-Q^+$, —$PO(O^-Q^+)_2$, —$P(O)(OR_2)_2$, —$SO_2$—$R_2$, —CO—NH—$R_2$, —$CONH_2$, $COOR_2$ or $Si(Me)_3$, wherein $Q^+$ is $H^+$, ammnonium or an alkali metal cation;
- if n is 2,
- $R_1$ is $C_1\text{–}C_{18}$alkylene, $C_3\text{–}C_{18}$alkenylene or $C_3\text{–}C_{18}$alkinylene, which may be unsubstituted or substituted by one or more OH, $C_1\text{–}C_8$alkoxy, carboxy or $C_1\text{–}C_8$alkoxycarbonyl;
- or xylylene; or
- $R_1$ is a bisacyl radical of an aliphatic dicarboxylic acid having 2 to 36 carbon atoms, or a cycloaliphatic or aromatic dicarboxylic acid having 8–14 carbon atoms;
- if n is 3,
- $R_1$ is a trivalent radical of an aliphatic, cycloaliphatic or aromatic tricarboxylic acid; and
- if n is 4,
- $R_1$ is a tetravalent radical of an aliphatic, cycloaliphatic or aromatic tetracarboxylic acid.

* * * * *